US010918291B2

(12) United States Patent
Rinderknecht et al.

(10) Patent No.: US 10,918,291 B2
(45) Date of Patent: Feb. 16, 2021

(54) PORTABLE ELECTRONIC HEMODYNAMIC SENSOR SYSTEMS

(71) Applicant: CALIFORNIA INSTITUTE OF TECHNOLOGY, Pasadena, CA (US)

(72) Inventors: Derek Rinderknecht, Arcadia, CA (US); Niema Pahlevan, Pasadena, CA (US); Peyman Tavallali, Pasadena, CA (US); Morteza Gharib, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/826,559

(22) Filed: Nov. 29, 2017

(65) Prior Publication Data

US 2018/0206747 A1 Jul. 26, 2018

Related U.S. Application Data

(63) Continuation of application No. 15/006,926, filed on Jan. 26, 2016, now abandoned, which is a
(Continued)

(51) Int. Cl.
*A61B 5/024* (2006.01)
*A61B 5/0408* (2006.01)
(Continued)

(52) U.S. Cl.
CPC ...... *A61B 5/02427* (2013.01); *A61B 5/02028* (2013.01); *A61B 5/0261* (2013.01);
(Continued)

(58) Field of Classification Search
CPC ........ A61B 5/02–5/0255; A61B 5/7235–5/725
(Continued)

(56) References Cited

U.S. PATENT DOCUMENTS

| 4,669,485 A | 6/1987 | Russell |
| 4,933,545 A * | 6/1990 | Saaski .................. G01L 9/0079 |
| | | 250/227.14 |

(Continued)

FOREIGN PATENT DOCUMENTS

| CN | 2765577 Y | 3/2006 |
| CN | 201492415 U | 6/2010 |

(Continued)

OTHER PUBLICATIONS

Heckman et al., Frequency analysis approach to the origin of the first and second heart sounds, 1982, American Heart Journal, 104:1309-1318.*

(Continued)

*Primary Examiner* — Jonathan T Kuo
(74) *Attorney, Agent, or Firm* — Knobbe Martens Olson & Bear, LLP

(57) ABSTRACT

Systems and methods are provided for extracting hemodynamic information, optionally employing portable electronic devices with optional User Interface (UI) features for system implementation. The systems and methods may be employed for acquiring hemodynamic signals and associated electrophysiological data and/or analyzing the former or both in combination to yield useful physiological indicia or results. Such hardware and software is advantageously used for non-invasively monitoring cardiac health.

21 Claims, 12 Drawing Sheets

Related U.S. Application Data continuation of application No. 14/601,170, filed on Jan. 20, 2015, now abandoned.

(60) Provisional application No. 61/992,044, filed on May 12, 2014, provisional application No. 61/992,035, filed on May 12, 2014, provisional application No. 61/932,576, filed on Jan. 28, 2014, provisional application No. 61/929,880, filed on Jan. 21, 2014.

(51) Int. Cl.
    *A61B 5/026*      (2006.01)
    *A61B 5/0402*      (2006.01)
    *A61B 5/02*      (2006.01)
    *A61B 5/00*      (2006.01)
    *A61B 7/04*      (2006.01)
    *A61B 7/02*      (2006.01)
    *A61B 5/0285*      (2006.01)
    *A61B 5/021*      (2006.01)

(52) U.S. Cl.
    CPC .......... *A61B 5/0402* (2013.01); *A61B 5/0408* (2013.01); *A61B 5/6898* (2013.01); *A61B 7/02* (2013.01); *A61B 7/04* (2013.01); *A61B 5/0002* (2013.01); *A61B 5/0059* (2013.01); *A61B 5/021* (2013.01); *A61B 5/024* (2013.01); *A61B 5/0285* (2013.01); *A61B 5/6822* (2013.01); *A61B 5/725* (2013.01); *A61B 5/7275* (2013.01); *A61B 5/742* (2013.01); *A61B 2560/0431* (2013.01)

(58) Field of Classification Search
    USPC ........................................................ 600/527
    See application file for complete search history.

(56) References Cited

U.S. PATENT DOCUMENTS

| | | | |
|---|---|---|---|
| 4,976,268 A | 12/1990 | Kurosawa et al. | |
| 4,991,197 A | 2/1991 | Morris | |
| 5,086,776 A * | 2/1992 | Fowler, Jr. ............ | A61B 5/0205 600/452 |
| 5,146,083 A | 9/1992 | Zuckerwar et al. | |
| 5,265,615 A | 11/1993 | Frank et al. | |
| 5,309,916 A | 5/1994 | Hatschek | |
| 5,363,855 A | 11/1994 | Drzewiecki et al. | |
| 5,411,028 A | 5/1995 | Bonnefous | |
| 6,135,957 A | 10/2000 | Cohen-Bacrie et al. | |
| 6,245,022 B1 | 6/2001 | Archibald et al. | |
| 6,477,406 B1 | 11/2002 | Turcott | |
| 6,483,929 B1 * | 11/2002 | Murakami ......... | G06K 9/00496 340/5.83 |
| 6,491,647 B1 * | 12/2002 | Bridger ................. | A61B 5/021 128/900 |
| 6,676,608 B1 | 1/2004 | Keren | |
| 6,738,734 B1 | 5/2004 | Huang | |
| 7,272,431 B2 | 9/2007 | McGrath | |
| 7,344,502 B2 | 3/2008 | Tanabe | |
| 7,361,148 B2 * | 4/2008 | Narimatsu ............ | A61B 5/022 600/490 |
| 7,811,234 B2 | 10/2010 | McGrath | |
| 7,889,053 B2 | 2/2011 | McGrath et al. | |
| 8,033,996 B2 | 10/2011 | Behar | |
| 8,232,866 B2 | 7/2012 | McGrath et al. | |
| 8,435,181 B2 | 5/2013 | Yang et al. | |
| 9,026,193 B2 * | 5/2015 | Pahlevan ............ | A61B 5/0004 382/128 |
| 9,480,406 B2 | 11/2016 | Pahlevan et al. | |
| 2002/0107450 A1 | 8/2002 | Ogura | |
| 2003/0069508 A1 | 4/2003 | Kawaguchi et al. | |
| 2003/0220577 A1 | 4/2003 | Bartels et al. | |
| 2003/0135124 A1 | 7/2003 | Russell | |
| 2003/0191400 A1 | 10/2003 | Shalman et al. | |
| 2004/0088123 A1 | 5/2004 | Ji | |
| 2004/0158162 A1 * | 8/2004 | Narimatsu ............ | A61B 5/022 600/494 |
| 2004/0260193 A1 * | 12/2004 | LaSala ................... | A61B 7/04 600/528 |
| 2005/0143667 A1 | 6/2005 | Park et al. | |
| 2007/0016031 A1 | 1/2007 | Mourad et al. | |
| 2007/0185391 A1 | 8/2007 | Morgan | |
| 2007/0210786 A1 | 9/2007 | Allen et al. | |
| 2007/0238995 A1 | 10/2007 | Sui et al. | |
| 2008/0234568 A1 | 9/2008 | Ouchi | |
| 2009/0018422 A1 | 1/2009 | Banet et al. | |
| 2009/0204012 A1 | 8/2009 | Joeken | |
| 2010/0185084 A1 | 7/2010 | Zhang | |
| 2011/0015496 A1 | 1/2011 | Sherman et al. | |
| 2011/0040181 A1 | 2/2011 | Yokota et al. | |
| 2011/0130800 A1 | 6/2011 | Weinstein et al. | |
| 2011/0224529 A1 | 9/2011 | Lading | |
| 2011/0275936 A1 | 11/2011 | Cho et al. | |
| 2012/0143068 A1 | 6/2012 | Cheng et al. | |
| 2012/0146796 A1 | 6/2012 | Margon et al. | |
| 2012/0238834 A1 | 9/2012 | Hornick | |
| 2012/0289848 A1 | 11/2012 | Li et al. | |
| 2013/0078095 A1 | 3/2013 | Olesen | |
| 2013/0172723 A1 | 7/2013 | Baxi et al. | |
| 2013/0184573 A1 * | 7/2013 | Pahlevan ............ | A61B 5/0004 600/430 |
| 2014/0073969 A1 * | 3/2014 | Zou ..................... | A61B 5/02108 600/479 |
| 2014/0330335 A1 | 11/2014 | Errico et al. | |
| 2015/0018635 A1 * | 1/2015 | Dinesen ................... | A61B 7/00 600/301 |
| 2015/0038856 A1 * | 2/2015 | Houlton ............... | A61B 5/0402 600/484 |
| 2015/0282695 A1 | 10/2015 | Tay et al. | |
| 2015/0297105 A1 | 10/2015 | Pahlevan et al. | |

FOREIGN PATENT DOCUMENTS

| | | | |
|---|---|---|---|
| EP | 1279370 A1 * | 1/2003 | ............... A61B 7/00 |
| JP | 2002-065677 | 3/2002 | |
| JP | 2004-305268 | 11/2004 | |
| JP | 2004305268 A * | 11/2004 | |
| KR | 10-2002-0055362 | 7/2002 | |
| KR | 10-2003-0070315 | 8/2003 | |
| KR | 10-2006-0004931 | 1/2006 | |
| WO | WO 2012/011029 | 1/2012 | |
| WO | WO 2012149652 | * 11/2012 | |

OTHER PUBLICATIONS

Suzuki, JP 2004305268 A, Google English Translation (Year: 2004).*
Wikipedia, Low-pass filter, 2020; https://en.wikipedia.org/wiki/Low-pass_filter (Year: 2020).*
EP, 13829710.6 Extended Search Report, dated Mar. 1, 2016.
EP, 15740487.2 Supplementary Search Report, dated Aug. 8, 2017.
EP, 15740738.8 Supplementary Search Report, dated Jul. 24, 2017.
WO, PCT/US2012/069947 ISR and Written Opinion, dated Feb. 27, 2013.
WO, PCT/US2012/071452 ISR and Written Opinion, dated Mar. 14, 2013.
WO, PCT/US2013/053068 ISR and Written Opinion, dated Nov. 26, 2013.
WO, PCT/US2013/054529 ISR and Written Opinion, dated Nov. 27, 2013.
WO, PCT/US2014/061256 ISR and Written Opinion, dated Jan. 22, 2015.
WO, PCT/US2015/012293 ISR and Written Opinion, dated Apr. 30, 2015.
WO, PCT/US2015/012096 ISR and Written Opinion, dated Jun. 29, 2015.
Abbas, A. E., et al., "Echocardiographic Determination of Mean Pulmonary Artery Pressure", The American Journal of Cardiology, 2003, vol. 92, pp. 1373-1376.

(56) References Cited

OTHER PUBLICATIONS

Angtuaco, M. J., et al., "Noninvasive Estimation of Diastolic Pulmonary Artery Pressure by Doppler Analysis of Tricuspid Regurgitation Velocity in Pediatric Patients", Congent. Heart Dis., 2011, pp. 1-8.
Cremer, A., et al., "Determination of central blood pressure by a noninvasive method (brachial BP and QKD interval)", J. Hypertens., 2012, vol. 30, pp. 1-7.
Daubechies, I., "The Wavelet Transform, Time-Frequency Localization and Signal Analysis", IEEE Transactions on Information Theory, 1990, vol. 36, No. 5, pp. 961-1005.
Denardo, S.J., et al., "Pulse Wave Analysis of the Aortic Pressure Waveform in Severe Left Ventricular Systolic Dysfunction", Circ Heart Fail, 2010, vol. 3, pp. 149-156.
Feng, J., et al., "Determination of wave speed and wave separation in the arteries using diameter and velocity", Journal of Biomechanics, 2010, vol. 43, pp. 455-462.
Fletcher, R. R., et al., "Clip-on wireless wearable microwave sensor for ambulatory cardiac monitoring", IEEE, 2010, pp. 365-369.
Friedberg, M. K., et al., "A Novel Echocardiographic Doppler Method for Estimation of Pulmonary Arterial Pressures", J. Am. Soc. Echocard., 2006, pp. 559-562.
Greenfiled, JR., J. C., et al., "Relation between pressure and diameter in main pulmonary artery of man", J. Appl. Physiol., 1963, vol. 18, No. 3, pp. 557-559.
Harada, A., et al., "Development of a Non-invasive Real-time Measurement System of Wave Intensity", IEEE Ultrasonics Symposium, 2000, pp. 1517-1520.
Hassan, S., et al., "Systolic time intervals: a review of the method in the non-invasive investigation of cardiac function in health, disease and clinical pharmacology", Postgraduate Medical Journal, 1983, vol. 59, pp. 423-434.
Heckman, J. L., et al., "Frequency analysis approach to the origin of the first and second heart sounds", American Heart Journal, 1982, vol. 104, pp. 1309-1318.
Hou, T.Y. et al., "Adaptive Data Analysis via Sparse Time-Frequency Representation", Advances in Adaptive Data Analysis, 2011, vol. 3, Nos. 1 & 2, pp. 1-28.
Hou, T.Y. et al., "Data-driven time-frequency analysis", Appl. Comput. Harman. Anal., 2013, vol. 35, pp. 284-308.
Huang, N.E., et al., "The empirical mode decomposition and the Hilbert spectrum for nonlinear and non-stationary time series analysis", Proc. R. Soc. Lond. A, 1998, vol. 454, pp. 903-995.
Huang, W., et al., "Use of intrinsic modes in biology: Examples of indicial response of pulmonary blood pressure to ± step hypoxia", Proc. Natl. Acad. Sci. USA, 1998, vol. 95, pp. 12766-12771.
Khir, A. W., et al., "Wave intensity I the ascending aorta: effects of arterial occlusion", Journal of Biomechanics, 2005, vol. 38, pp. 647-655.
Lanzarini, L., et al., "Noninvasive estimation of both systolic and diastolic pulmonary artery pressure from Doppler analysis of tricuspid regurgitant velocity spectrum in patients with chronic heart failure", American Heart Journal, 2002, vol. 144, pp. 1087-1094.
Lee, J. Y., et al., "A Microprocessor-Based Noninvasive Arterial Pulse Wave Analyzer", IEEE Transactions on Biomedical Engineering, 1985, vol. BME-32, No. 6, pp. 451-455.

Milan, A., et al., "Echocardiographic Indexes for the Non-Invasive Evaluation of Pulmonary Hemodynamics", J. Am. Soc. Echocard., 2010, vol. 23, No. 3, pp. 225-239.
Olijhoek, J. K., et al., "The Metabolic Syndrome is associated with advanced vascular damage in patients with coronary heart disease, stroke, peripheral arterial disease or abdominal aortic aneurysm", European Heart Journal, 2004, vol. 25, No. 4, pp. 342-348.
Pahlevan, N.M., et al., "A Physiologically Relevant, Simple Outflow Boundary Model for Truncated Vasculature", Annals of Biomedical Engineering, 2011, vol. 39, No. 5, pp. 1470-1481.
Pahlevan, N.M., et al., "Low pulse pressure with high pulsatile external left ventricular power: Influence of aortic waves", Journal of Biomechanics, 2011, vol. 44, No. 11, pp. 2083-2089.
Pahlevan, N.M., et al., "Aortic Wave Dynamics and Its Influence on Left Ventricular Workload", PLoS ONE, 2011, vol. 6, No. 8, pp. 1-8.
Pahlevan, N.M., et al., "A Bio-Inspired Approach for the Reduction of Left Ventricular Workload", PLoS ONE, 2014, vol. 9, No. 1, pp. 1-12.
Pahlevan, N.M., et al., "Intrinsic frequency for a systems approach to haemodynamic waveform analysis with clinical applications", Journal of the Royal Society Interface, 2014, vol. 11, pp. 1-10.
Patel, D. J., et al., "Mechanical properties and dimensions of the major pulmonary arteries", J. Appl. Physiol., 1960, vol. 15, No. 1, pp. 92-96.
Schiffrin, E. L., "Vascular Stiffening and Arterial Compliance: Implications for Systolic Blood Pressure", The American Journal of Hypertension, 2004, vol. 17, No. 12, Part 2, pp. 39S-48S.
Selton-Suty, C., et al., "Non-invasive investigations of the right heart: How and why?", Archives of Cardiovascular Disease, 2009, vol. 102, pp. 219-232.
Singh, A., et al., "Pulse Pressure Monitoring Through Non-Contact Cardiac Motion Detection Using 2.45 GHz Microwave Doppler Radar", Engineering In Medicine and Biology Society, 33rd Annual International Conference of the IEEE EMBS, Boston, Massachusetts, USA, Aug. 30-Sep. 3, 2011.
Stehouwer, C. D. A., et al., "Arterial stiffness in diabetes and the metabolic syndrome: a pathway to cardiovascular disease", Diabetologia, 2008, vol. 51, pp. 527-539.
Stoner, L., et al., "Relationship between blood velocity and conduit artery diameter and the effects of smoking on vascular responsiveness", J. Appl. Physiol., 2004, vol. 96, pp. 2139-2145.
Sugawara, M., et al., "Clinical usefulness of wave intensity analysis", Med. Biol. Eng. Comput., 2009, vol. 47, pp. 197-206.
Swillens, A., et al., "Effect of an Abdominal Aortic Aneurysm on Wave Reflection in the Aorta", IEEE Transactions on Biomedical Engineering, 2008, vol. 55, No. 5, pp. 1602-1611.
Van Den Wijngaard, J. P.H.M., et al., "Comparison of arterial waves derived by classical wave separation and wave intensity analysis in a model of aortic coarctation", Med. Biol. Eng. Comput., 2009, vol. 47, pp. 211-220.
Wikipedia, Cardiac cycle, published Nov. 14, 2012.
Yokobori, JR., A. T., et al., "The Analysis and Diagnosis of Unstable Behavior of the Blood Vessel Wall with an Aneurysm Based on Noise Science", Journal of Atherosclerosis and Thrombosis, 2006, vol. 13, No. 4, pp. 163-174.

* cited by examiner

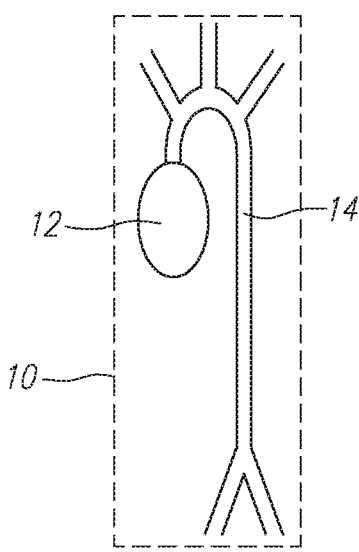
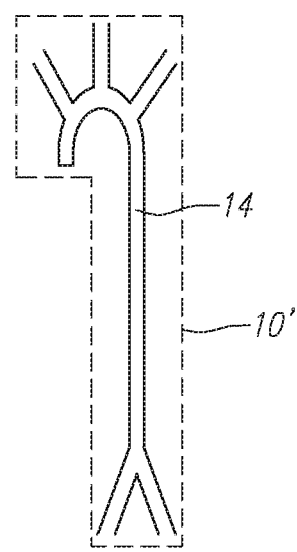
FIG. 1A  FIG. 1B
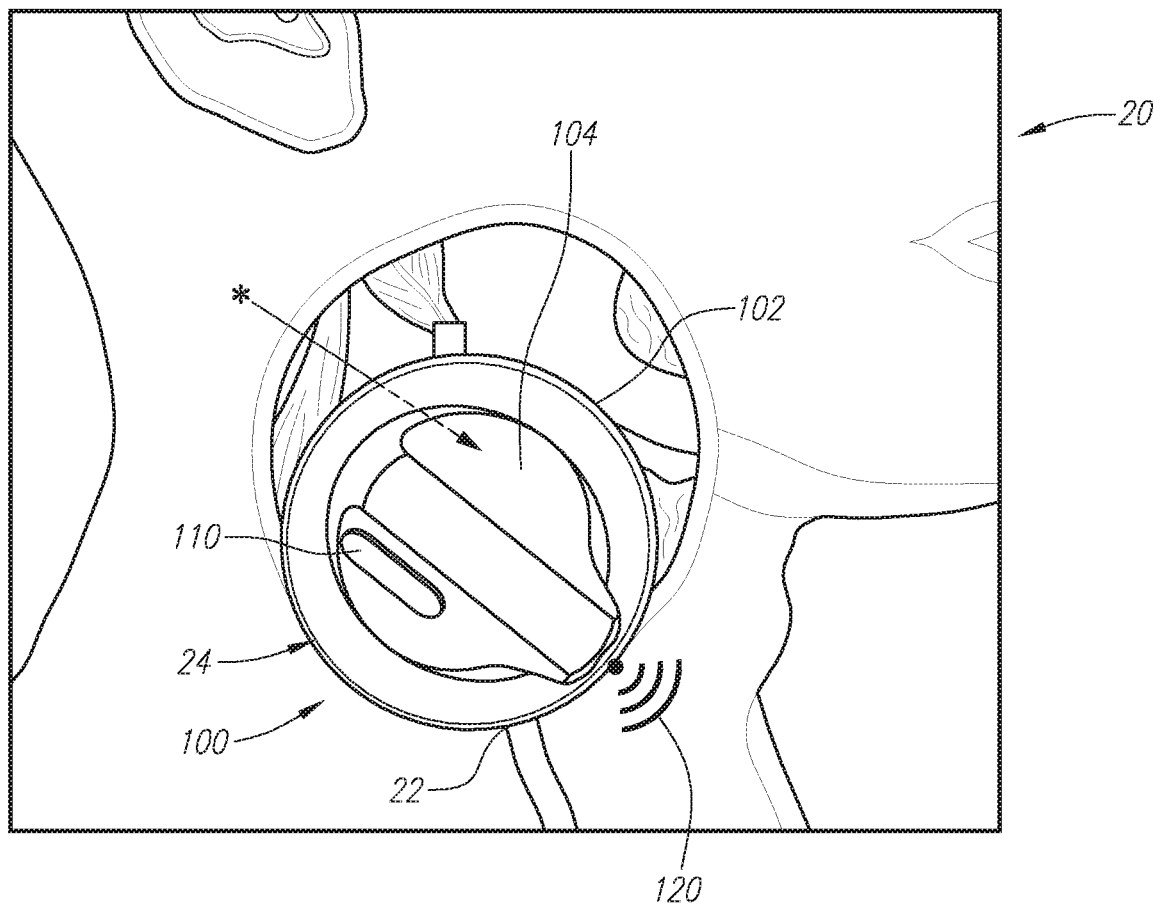
FIG. 2

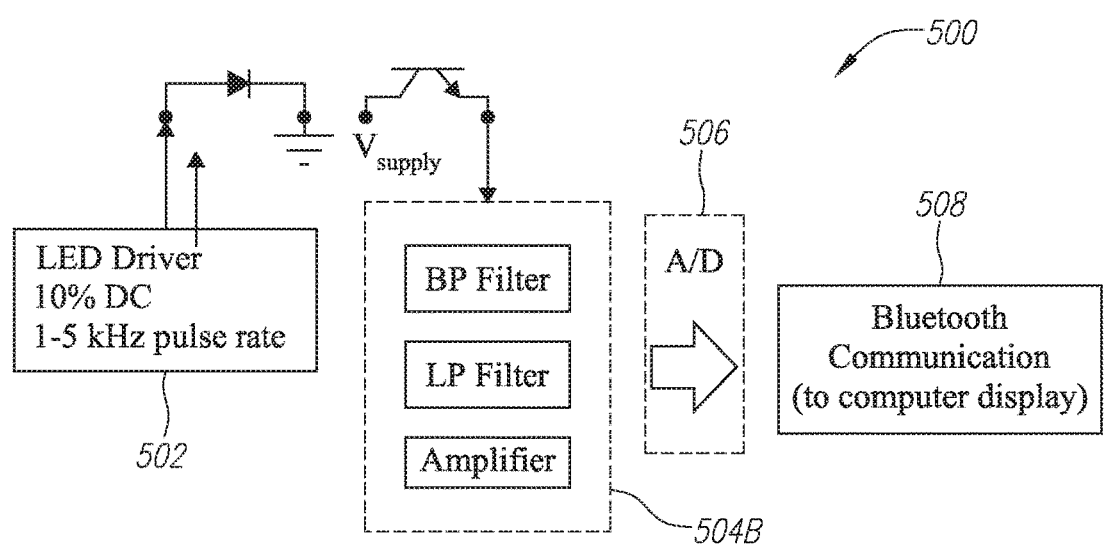
FIG. 10B
FIG. 11A          FIG. 11B

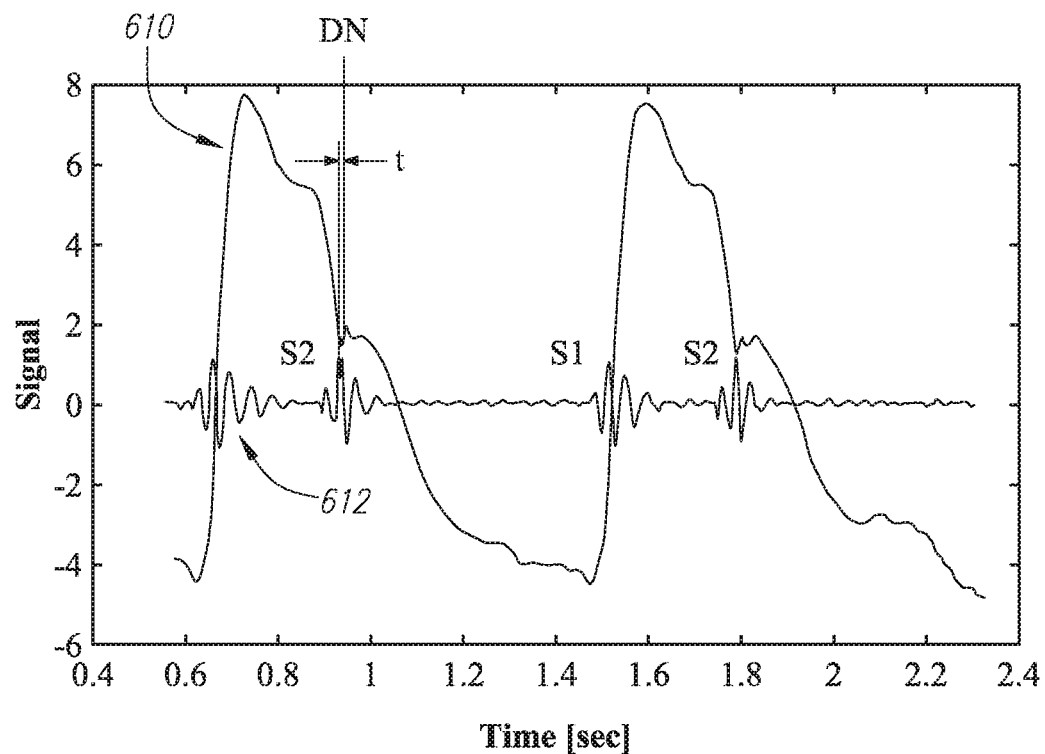
FIG. 13A
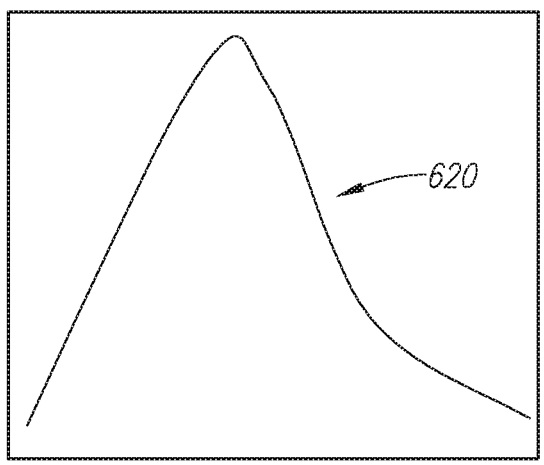 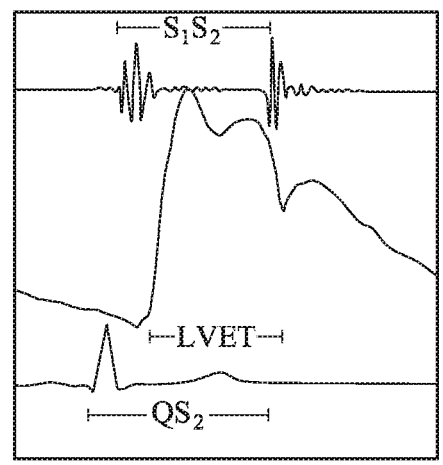
FIG. 13B          FIG. 13C

PORTABLE ELECTRONIC HEMODYNAMIC SENSOR SYSTEMS

RELATED APPLICATIONS

This filing is a continuation application of U.S. patent application Ser. No. 15/006,926, filed Jan. 26, 2016, which is a continuation application of U.S. patent application Ser. No. 14/601,170, filed Jan. 20, 2015, now abandoned, which claims the benefit of and priority to U.S. Provisional Patent Application Ser. No. 61/929,880, filed Jan. 21, 2014, Ser. No. 61/932,576, filed Jan. 28, 2014, Ser. No. 61/992,035, filed May 12, 2014, and Ser. No. 61/992,044, filed May 12, 2014, all of which are incorporated by reference herein in their entireties and for all purposes.

FIELD

The present subject matter relates to devices and methods for obtaining and utilizing hemodynamic waveform measurements.

BACKGROUND

Cardiovascular diseases (CVDs) are the underlying cause of about one of every three deaths in United States each year. About 34% of American adults are suffering from one or more types of CVD. In 2010, the total direct and indirect cost of CVDs was approximately $503 billion.

There is an urgent need to develop new methods and devices for diagnosing and monitoring CVDs. Diagnosis enables early intervention and remediation. Monitoring is a useful tool in behavior modification and in the prediction and subsequent avoidance of acute events that can lead to emergency hospitalization, morbidity, and/or mortality. New methods and devices to meet these need(s) advantageously enable extracting hemodynamic information from or in connection with a portable electronic device.

SUMMARY

Example embodiments of systems and methods are provided for acquiring and/or utilizing hemodynamic information, optionally, in connection with portable electronic devices. As such, a portable approach for the quantification of cardiovascular physiology and diagnosis of cardiovascular disease (CVD) is provided that can operate utilizing a mobile communication device (e.g., smartphone) platform. An optional User Interface (UI) and/or other features adapted for hemodynamic signal acquisition may be incorporated for system implementation.

In certain system embodiments, a smartphone, a hardware-modified smartphone, a peripheral instrument or sensor(s) wired or wirelessly connected to a smartphone, or other portable electronic devices can be used to obtain physiological waveform data. Once a physiological waveform has been acquired, the data can be stored locally or on a server (e.g., the "Cloud"). The waveform may be analyzed remotely (e.g., by or in the Cloud) or locally.

Certain calculations involving the waveform(s) may employ an Intrinsic Frequency (IF) method, a sparse time frequency representation (STFR) algorithm, or any other empirical mode decomposition based method. Other approaches are referenced below as well.

Various physiological parameters may be calculated from the obtained physiological waveform(s). In one embodiment, left ventricular Ejection Fraction (EF) can be calculated and displayed to the user. In another embodiment, Stroke Volume (SV) and/or Cardiac Output (CO) can be calculated. For either such determination, see U.S. patent application Ser. No. 14/517,702, filed Oct. 17, 2014, and titled, "INTRINSIC FREQUENCY ANALYSIS FOR LEFT VENTRICLE EJECTION FRACTION OR STROKE VOLUME DETERMINATION," incorporated by reference herein in its entirety and for all purposes. Another approach to determining EF may be adapted from "The Relationship of Alteration in Systolic Timer Intervals to the Ejection Fraction in Patients with Cardiac Disease," *Circulation.* 1970; 42: 455-462 with related systolic time intervals determined by reference to "Systolic Time Intervals in Heart Failure in Man," *Circulation.* 1968; 37:149-159 and "The Relationship of Alterations in Systolic Time Intervals to Ejection Fraction in Patients with Cardiac Disease," Circulation. 1970; 42: 455-462, both of which are incorporated by reference herein in their entirety for all purposes. In yet another example embodiment, IF values ($\omega_1$, $\omega_2$) are calculated and a health status determination can be displayed. For such determinations, see U.S. Patent Publication No. 2013/0184573, also incorporated by reference herein in its entirety for all purposes.

The embodiments described herein can obtain electrocardiogram (i.e., EKG or ECG), phonocardiogram, and arterial pulse waveforms. These embodiments can include an optical sensor for the measurement of the arterial pulse waveform and/or heart sound. Optical detection may be accomplished by a LED or photodiode combination. In another embodiment, a pulse wave may be recorded via microwaves. A microwave transceiver may be located behind the screen of the mobile communication device for such purpose.

Regarding specific hardware implementations, one example embodiment involves quantification of cardiovascular physiology and diagnosis of CVD utilizing a standard smartphone platform (typically in connection with customized hardware and/or software). These embodiments exploit the analog signal from a camera in combination with the camera LED flash to measure the reflectance of light off the skin in the proximity of an artery passing near the surface of the skin to quantify its radial expansion in response to a time varying blood pressure. Such an approach optionally involves a series of components: using a camera integrated in a portable electronic device to record the motion of the skin to capture the shape of the blood pressure waveform, user feedback provided through visual and/or auditory signal(s) enabling the enhancement of signal quality, and the design of the data display and analysis. Although the approach is described herein in terms of cardiovascular waveforms, a variety of waveforms can be analyzed employing such a platform.

In certain embodiments where such systems are used, a user locates a pulse where a major arterial passes near the surface of the skin and places the phone such that the camera and LED both image and illuminate the location respectively. A prepare screen then begins to display the relative motion of the skin. In one embodiment, the average intensity of the camera signal is used to create a signal describing the relative motion of an artery. In another embodiment, only particular regions of the camera image are subjected to averaging, although more elaborate image processing schemes are possible for such information as known by those skilled in the art that may be applied hereto. In addition, the device's LED intensity may be adjusted to maintain an adequate signal-to-noise ratio for the waveforms being acquired by the device. The LED may also be strobed in a manner that cuts down on noise (e.g., by offsetting from or screening out other frequencies where noise is present). For example, the LED can be pulsed at a frequency above what common electronics use. In some embodiments, the LED strobing frequency may be between 500 Hz and 1 GHz or more preferably in the range of 2 kHz to 64 kHz.

In another embodiment, the waveform may be obtained through a peripheral instrument such as a wired pulse oximeter. Indeed, the waveform may be acquired through any of microwave, strain-gauge, piezoresistive, capacitive, optical, or acoustic sensors. A combination or multiplexing of sensors may be used. For example, an array of LEDs and detectors camera or photodetectors may be used to analyze the motion of the skins surface. In one embodiment the detector is a phototransistor. In another embodiment, the detector is a photodiode. Such instruments may be connected through a microphone jack to a/the smartphone. In some embodiments, the peripheral instruments are connected wirelessly such as through WiFi or BLUETOOTH.

To accommodate different body types, a probe-style peripheral sensor (e.g., in a stethoscope-type shape) with a detector and an array of LEDs may be used. Such a probe may also be adapted to perform an ECG. The probe may include one or more ECG sensor contacts leads or electrodes on the probe head for such purposes. In another embodiment, the probe has one or more ECG electrodes on the probe head and at least one additional electrode on a grip portion, thereby providing an increased measurement path if the device is held in position by the user. In another embodiment, the probe has a secondary connection to add an additional ECG electrode for the case where an operator is holding the device for the subject. In this case, the grip portion ECG electrode is optionally deactivated.

The above offers an example of a so-called "multiplexing sensor." Another embodiment includes a waveform detecting sensor, ECG electrodes and a microphone combined into a peripheral data probe. This or another probe may also measure blood pressure, hydration, skin impedance, temperature, the waveform as well as a phonocardiogram.

In another embodiment, the sensor device is enclosed in a specialized case to enhance waveform acquisition (e.g., as in the example of smartphone hardware). This case may integrate a multitude of sensors. The case may include optical components such as lenses allowing the location and direction of the incoming optical signal to be adjusted according to body type and skin rigidity. Case hardware may also be provided to set a standoff distance for the device camera and LED that are adjustable between about 10 µm to about 10 cm. A mechanical add-on to the device case (or directly to the smartphone) may be provided to enable relative positioning and/or tensioning of the skin.

In one example of skin tensioning hardware, a ring with various deflectable, deformable and/or stop features as detailed below may be employed. In another example, a sensor membrane may be provided in the (optical) sensor system. The membrane may comprise any number of plastics, animal skin, and/or rubber. A polyester or polyurethane membrane may be preferred.

Whether employed in connection with skin-tensioning hardware configurations or adaptations or merely as a sensor interface in use, the membrane is located or placed in contact with the skin where signal acquisition is desired (i.e., between the optical sensor and the skin). The thickness of the membrane and material from which it constructed (e.g., rubber, plastic, metal or composite material) is chosen to exhibit mechanical properties that allow the membrane to follow the underlying pulse waveform and record the same. As such, the membrane may have a thickness is in the range of about 12 to about 500 The membrane may cover a diameter ranging from 1 mm to 50 mm. The optical properties of the membrane may be chosen such that it reflects at the wavelengths of the LED incorporated in the smartphone (or used in a separate device) and ambient light to otherwise decrease signal noise. It may be optically opaque at the wavelength or wavelengths of detection.

Indeed, the membrane serves a number of functions such as normalizing for subjects skin tone, acoustic coupling for phonocardiographic measurements as well as providing a sterile and disposable barrier for testing. In another embodiment, the membrane is not disposable.

When the membrane is disposable it may snap, press-fit, or screw in place. In another embodiment, the membrane is housed in another component that couples it to the handheld sensor device. The membrane may have a rigid frame. Use of such a membrane incorporated in a hemodynamic sensor device (as in a device for direct attachment to a smartphone and/or as incorporated in a stand-alone sensor embodiment) serves the purpose of increased robustness to user skin tone and body topography. As to further details of its operation of the membrane for use in pressure waveform monitoring in connection with a light source (be it an LED, laser or otherwise), these can be appreciated in reference to U.S. Pat. No. 5,363,855 incorporated herein by reference in its entirety for all purposes.

The membrane may have multiple regions with different or varying material properties. In another embodiment, additional constraints or structures may be used to enhance signal quality. In another embodiment, the device may not have a membrane.

In addition to picking up a pulse waveform from skin vibration caused by underlying arterial motion, the subject membrane-based sensor arrangement (including a light source and sensor for light reflected from the membrane) is able to detect a higher frequency range of vibrations corresponding to the so-called heart sounds. Notably, these sounds are offset in timing from heart sounds that can be detected over a subject's heart (i.e., in the region of the sternum).

The nature of heart sounds that may be detected at a peripheral locations were the subject of some study roughly half-a-century prior to the subject filing. Particularly, Farber et al., in "Conduction of Cardiovascular Sound Along Arteries," *Circ. Res.* 1963; 12:308-316, discussed the origin of heart sounds that may be detected at a peripheral location as well as their mode of propagation. The inventors hereof believe that those authors properly concluded that the heart sounds that may be detected at peripheral location(s) ride upon or are embedded with the blood pressure wave. Embodiments provided herein apply such information to practical use for complex calculation of physiological parameters.

In these embodiments, the heart sounds that are generated (i.e., resolved or separated as further discussed below) from the vibration signals obtained are referred to herein as Embedded Frequency signals or Embedded Frequencies. The heart sounds may be acquired optically and isolated by amplifying and filtering. The heard sounds may be isolated by high pass filtering the pulse waveform. The filtering may be achieved by mechanical filtering or by the response bandwidth of a transducer as in the case of a microphone.

As detailed further below, the properties and timing (especially its synchronicity relative to the pulse waveform) of the Embedded Frequency signals offers great utility in interpreting the features of the pulse pressure waveform and other possible utility heretofore unused and/or problematic to otherwise derive.

Additional embodiments hereof include various improved techniques for signal acquisition. These techniques may be integrated into the UI of the subject devices and/or accomplished through interaction with a peripheral marker, beacon or service. Any of these various audio and/or visual indicators discussed below may be regarded as various selectable signaling means.

In one set of examples, an auditory signal is assigned the information streaming from the camera in the sensor device platform. For example, each camera frame may be averaged and turned into a single instantaneous point, therefore a frame rate of 30 fps produces a (background auditory) signal of 30 Hz. In another embodiment, the camera or sensor acquisition rate ranges from 10 Hz to 100 kHz. In another embodiment, the auditory signal is produced by multiplying or modulating a background auditory signal such as white noise by the incoming data. In another embodiment, the time derivative of the incoming data is multiplied by a background auditory signal. In another embodiment, the incoming data is manipulated through a mathematical operator. In another embodiment, the background signal is brown noise, pink noise or of a single frequency. In another embodiment, the background sound is user customizable. In sum, the exact details or feel of the background auditory signal modulated by the physiological waveform data is left up to those skilled in the art. Nevertheless, the sound (i.e., background auditory signal) may be rescaled to still be audible for weak signals. The auditory cutoff for this sound may be used to indicate a minimum threshold for a usable signal.

In another set of examples for optimizing signal acquisition location, the user is prompted visually or audibly to move locations until the signal possesses a particular quality or span. This sound may have the recognizable character of a phonocardiogram. Such an auditory feedback signal may be used to allow the user to home in on the optimal location based on (audibly detected) waveform shape and intensity. Alternatively, the auditory feedback may take the form of a beep or similar noise. The frequency of beeping may increase as sensor device position is improved by the user to improve acquired signal quality. Once achieved, a position "lock" may be indicated by a constant tone.

In another embodiment, acquisition signal quality is indicated by an indicator light. This indicator may be an icon on the screen of a/the smartphone and/or peripheral device. Alternatively, the visual signal may take the form of a slide or meter. Such a meter may comprise a series of collinear dots or the meter may rotate like a clock or speedometer. Another such meter may comprise a target or series of concentric rings which are illuminated towards the center and/or flash in a similar pattern.

In another embodiment, signal quality indices are applied to screen the incoming physiological waveforms. These signal quality indices may be based on the timing, span, or shape of the waveform or combinations thereof. These indices may be used to communicate with the user to prompt improved positioning, retaking of data or other (re)action. Likewise, machine learning or neural network type algorithms may be utilized to screen poor waveforms and/or alert the user to properly acquired physiological waveform data.

In another embodiment, a locator system may be provided in connection with a physical marker or external device which has communicated or is in communication with the waveform acquisition system. Conventional positional triangulation techniques and RF or other signaling may be used for such purposes. In another embodiment, a directional microphone targeted to the location of maximum sensitivity of the camera may be used to detect the optimum location/position. In another embodiment, a focused LED or low power laser is used to roughly indicate the center of the sensor area to the user.

In yet another embodiment, locating the sensor device for optimal signal acquisition may be achieved in connection with a constant marker preferably not (although possibly) seen by the user. Such a marker may comprise an IR skin tag or IR tattoo viewable only to the camera and illuminated via the LED. In one embodiment, these are alignment marks indicating position as well as orientation. As another alternative, an injectable skin tag in the form of a small metallic or ferromagnetic component may be used. The injectable skin tag may comprise an RFID chip or other small electronic device.

More generally, embodiments hereof include systems (including the sensor hardware referenced herein and the addition of a computer processor and other ancillary/support electronics and various housing elements), methods (including software and associated hardware for carrying out specified acts) and UI features (including layouts and options and/or methodology associated with system use). Many of the subject device and/or system embodiments may be adapted for wearable as well as hand-held use.

BRIEF DESCRIPTION OF THE DRAWINGS

The figures provided herein may be diagrammatic and not necessarily drawn to scale, with some components and features exaggerated and/or abstracted for clarity. Variations from the embodiments pictured are contemplated. Accordingly, depiction of aspects and elements in the figures are not intended to limit the scope of the claims, except when such intent is explicitly stated.

FIGS. 1A and 1B are diagrams illustrating dynamic coupling of the heart and aorta in a human circulatory system.

FIG. 2 is a cutaway anatomical illustration showing device positioning for signal acquisition.

FIGS. 10A and 10B are schematics illustrating electronics of optical acquisition embodiments.

FIGS. 11A and 11B are diagrams of the anatomy interrogated for hemodynamic signal acquisition.

FIGS. 13A-13C are charts variously illustrating Embedded Frequency measurement and methodology.

DETAILED DESCRIPTION

Figure 3:
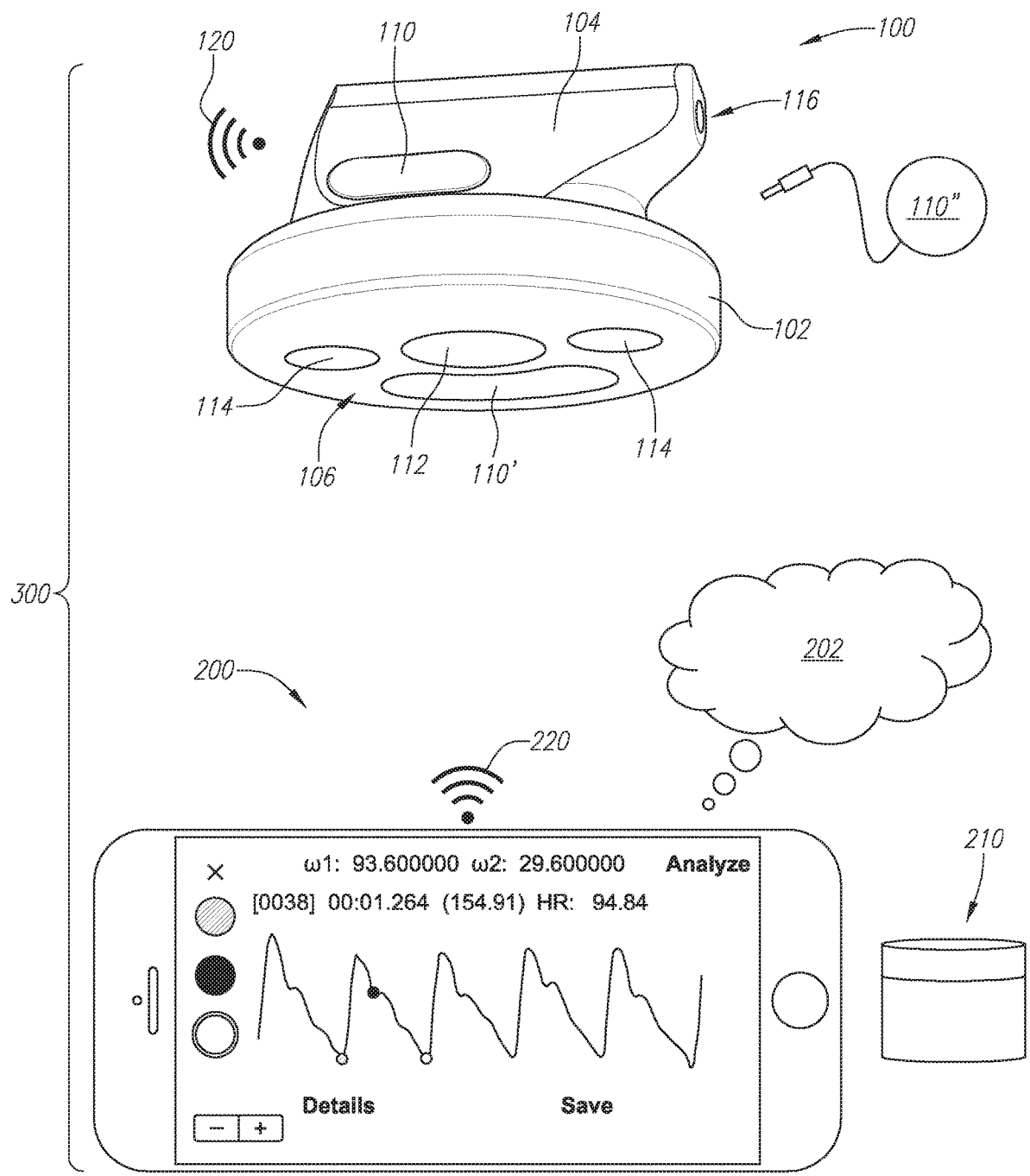
FIG. 3 is a system overview including exemplary hardware of one embodiment.

Various example embodiments are described below. Reference is made to these examples in a non-limiting sense. They are provided to illustrate more broadly applicable aspects of inventive aspects. Various changes may be made to the embodiments described and equivalents may be substituted without departing from their true spirit and scope. In addition, many modifications may be made to adapt a particular situation, material, composition of matter, process, process act(s) or step(s) to the objective(s), spirit or scope of the claims made herein.

As pertinent to certain measurement and calculations performed in connection with the subject systems, pressure and flow waves generated by the heart propagate in the compliant arterial vasculature. These waves are reflected at various reflection sites in the arterial system. The waves carry information about the heart, vascular system and coupling of heart and vasculature. As a result, extracting information from these waves is of great importance.

FIG. 1A illustrates a coupled heart-aorta system 10 in systole, with the aortic valve open (not shown) and blood being pumped by the heart 12 into the aorta 14. The heart and aorta construct a coupled dynamic system before the closure of the aortic valve. As shown in FIG. 1B, after aortic valve closure during diastole, the heart and aorta systems are decoupled in a second system state 10'. The aortic waves contain in each state include information about heart dynamics, arterial network dynamic and heart-aorta coupling. Extraction of such information by analysis enables a variety of determinations concerning cardiovascular health and/or various parameters as further discussed herein. The subject technologies are of use on obtaining hemodynamic wave form signals for such analysis and other analysis as may be desired.

As summarized above, various hardware, methodology or software and UI features (collectively, "technologies") are contemplated for the acquisition of hemodynamic waveform data. One set of these technologies involves sensor device configurations and/or processing for signal acquisition. Another set involves signal sampling location optimization technologies. Some of these technologies involve marking and/or locating techniques, the latter including UI-type feedback techniques. After the physiological data has been acquired and analyzed, it may variously yield indication or display (i.e., on the subject portable electronic device) instantaneous health status, heart ejection fraction, stroke volume and/or cardiac output.

Handheld Sensor Devices and Systems

FIG. 2 provides a view of a human user or subject 20 with a cutaway illustrating various anatomical features along with a handheld sensor device 100 targeting the common carotid artery 22, optionally around the carotid bifurcation 24 for hemodynamic waveform acquisition. For this purpose, a base 102 of the device may be separated from the skin by some distance. In one example, this "standoff" distance is about 1 mm. Although not shown, device 100 may be held by the subject 20 or another user employing handle interface 104.

This handheld sensor unit or device 100 may include an ECG electrode 110 associated with the handle (e.g., as discussed below). Signal acquisition status, prompts and/or other programming signals or instructions may be transmitted between handheld device 100 and other system components (as further described below or otherwise) via RF energy 120 in the form of WiFi, a BLUETOOTH signal or using another protocol.

As referenced further below, various UI features may be incorporated in the subject system(s). An associated element may be in the form of a marker affixed (as in a tattoo) or implanted (as in a biocompatible pellet or more complex device) at an optimal spot for signal acquisition as indicated by the asterisk ("*") in FIG. 2. Such a feature may simply indicate a target point. Alternatively, the marker feature may include a directional component for rotational registration. Such an approach may be implemented employing a rod, diamond-shaped or box-shaped marker body or indicator and/or a selected pattern applied to or implanted within the subject's skin. FIG. 3 describes an overall system 300 including a handheld sensor device 100, a smartphone unit 200 and an optional charger and/or sterilization unit 210 for device 100. As illustrated, smartphone 200 communicates with/between sensor device 100 employing signals 120/220 as in "paired" BLUETOOTH devices or via another protocol. The smartphone may receive information corresponding to a hemodynamic signal as further treated below. Such a signal may be stored and/or processed via connection with the Internet—as in so-called Cloud 202 computing.

Regarding further optional features of the handheld sensor device 100, its perspective view included in FIG. 3 yields additional details. Specifically, a face or facing surface 106 of base 102 incorporates additional sensors. These may include an ECG electrode 110', an optical sensor or sensor region 112 and/or microphone(s) 114. Optional use of two microphones allows for direction sound sensing for homing in on an improved or ideal signal sensing location. As another option, a plug or port 116 may be provided for connection to yet another ECG electrode 110" (for when the device is not held or operated by the user) or other peripheral hardware (e.g., head phones for the audio signal of a cardiophonogram (i.e., for auscultation). The handheld device 100 may be placed in a wireless charging station 210 for recharge. A UV sterilization system may be included with the wireless charger. In another embodiment, device 100 and its components (e.g., including a sensor membrane as discussed further below) may comprise materials compatible with ethanol sterilization.

Figure 4A:
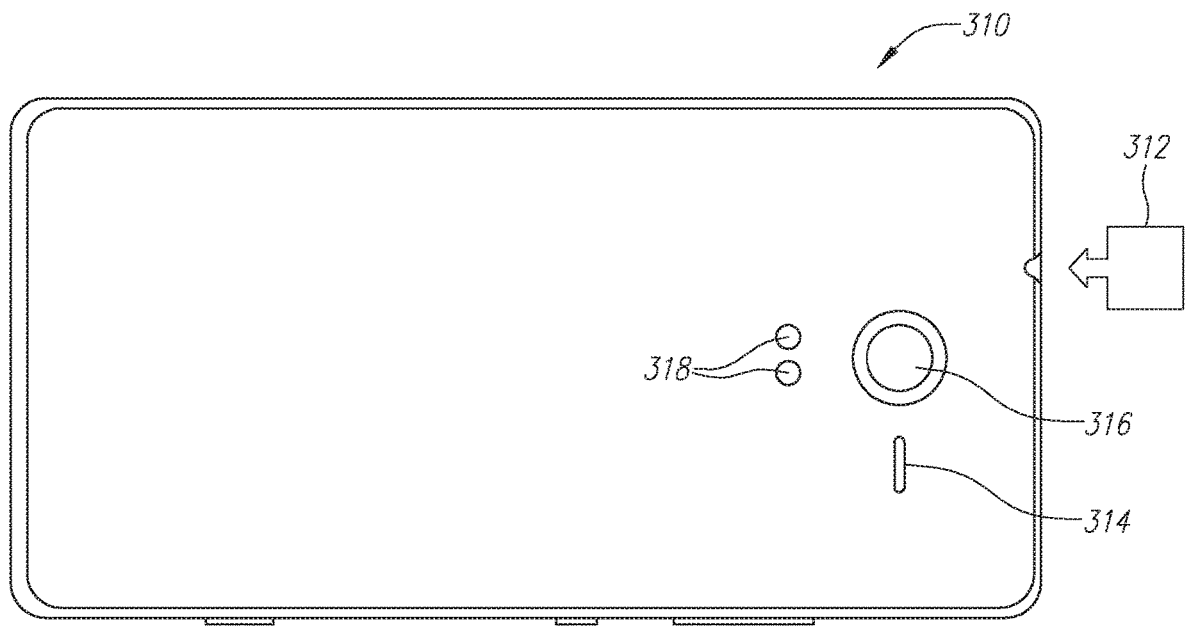
FIGS. 4A and 4B are opposite face-side views of smartphone hardware employed in another embodiment.
Figure 4B:
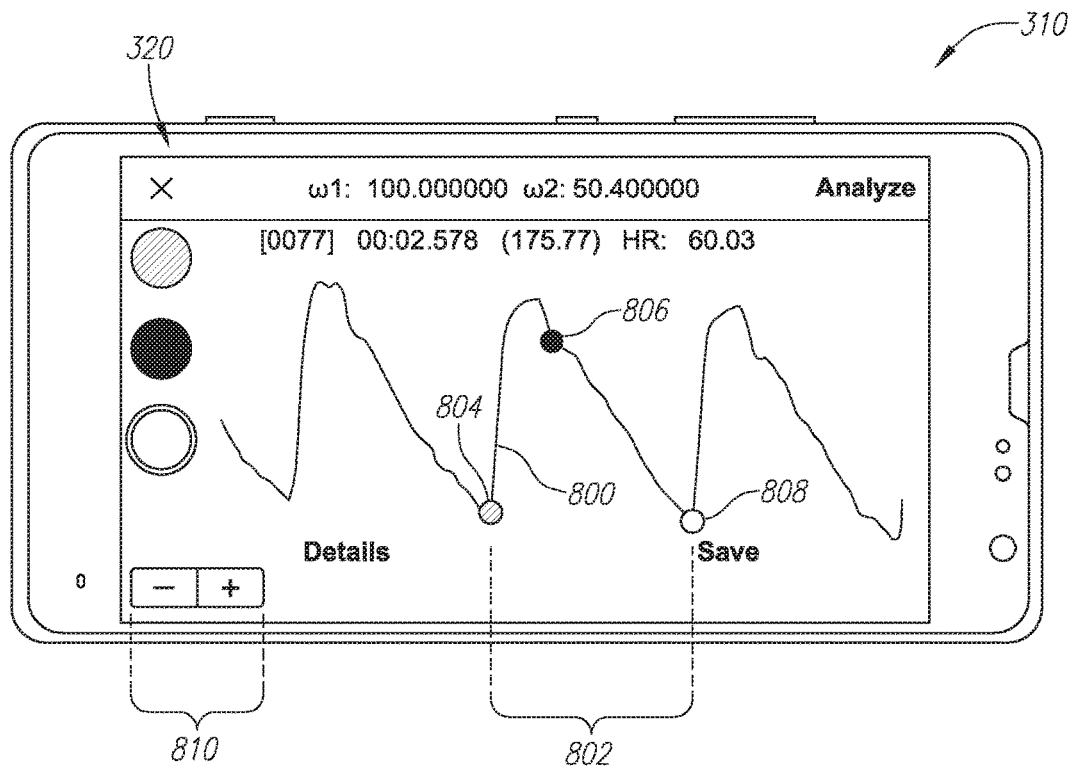

FIGS. 4A and 4B illustrate an approach in which the smartphone itself is used as the sensor means in a combined sensing and processing device 310. Various other peripheral components may be attached thereto as well. A direction microphone 312 may be so-connected. Or such a microphone 312 may complement a built-in microphone 314 to provide direction sound sensing.

In any case, the smartphone platform will typically include a camera sensor 316 and one or more LED light or "flash" element(s) 318. Or one such element may be a focused LED or low power laser used to roughly indicate the center of the sensor area to the user. In any case, with the camera and incorporated lighting system(s), the device is able to sense and capture a hemodynamic waveform. Such information may be further processed and depicted as shown in FIG. 4B on screen or display 320 and further commented on below.

Figure 5A:
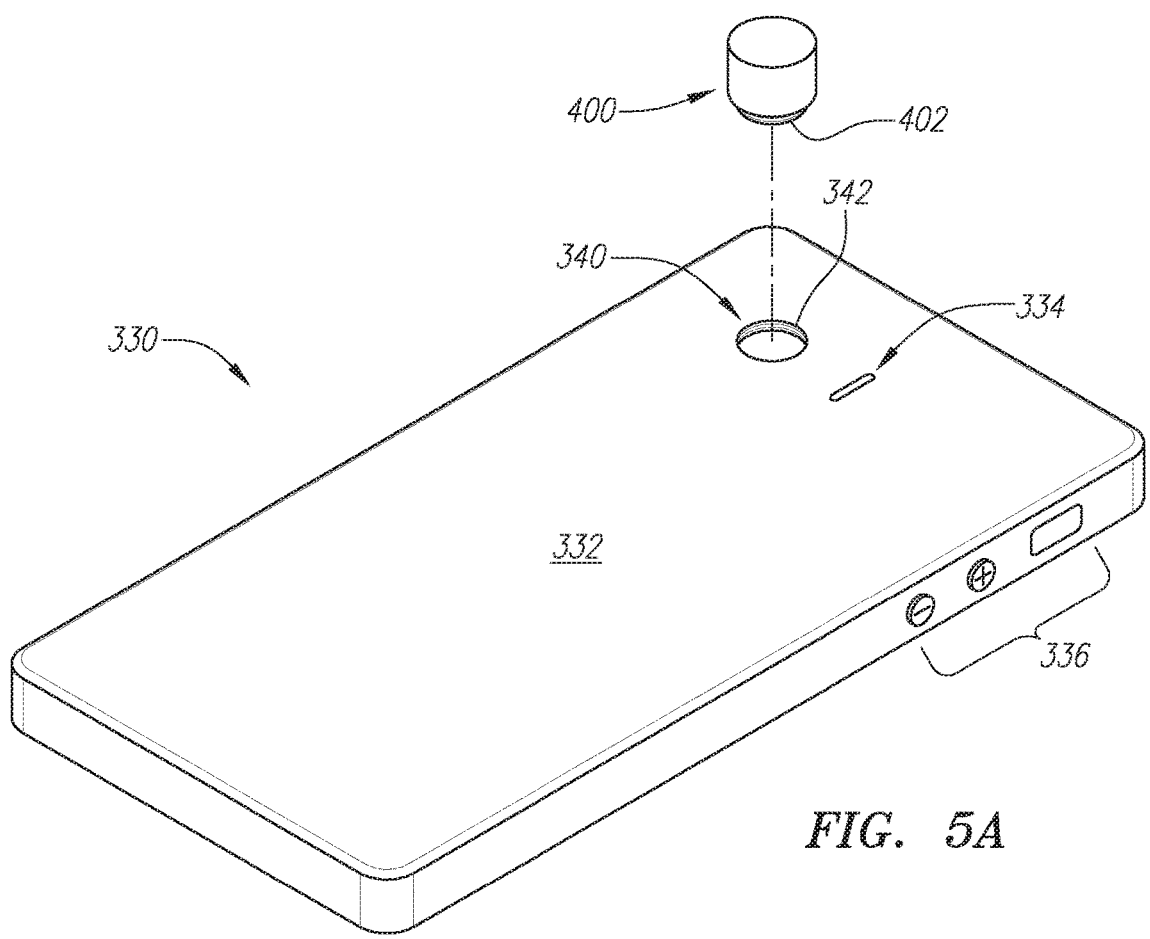
FIGS. 5A and 5B are opposite-facing oblique views of a specialized smartphone case hardware and associated hardware that may be employed in another embodiment.
Figure 5B:
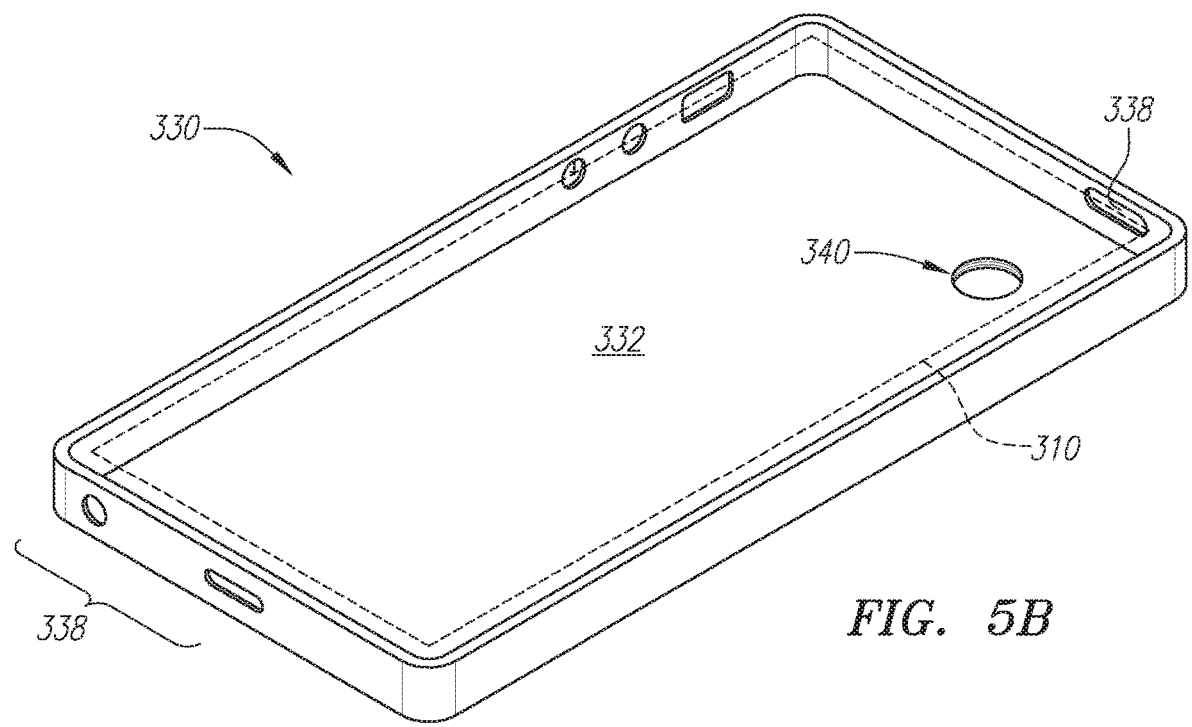

Device 310 may be received (as indicated by dashed line) within a case 330 such as shown in FIGS. 5A and 5B. Features of such a case may include an adjustable standoff feature and/or an amplification ring structure 400. This structure may include screw-in, twist-and-lock or snap attachment features 402 to secure the amplification ring to the device or device case. The ring may also include optics to further enhance the detection qualities of the smartphone. Around a window or aperture 340 for camera or sensor optics, case 330 may include amplification sub-system interface features 342 complementary to features 402.

As a body 332 of the case will typically be adapted for a given model of smartphone, its camera aperture 340 and a flash or LED aperture 334, volume and/or lock interfaces or clearances 336 and various connector through holes 338 will be so-configured. This body (and/or its constituent parts) may comprise plastic or any other conventionally used smartphone case material.

Figure 6:
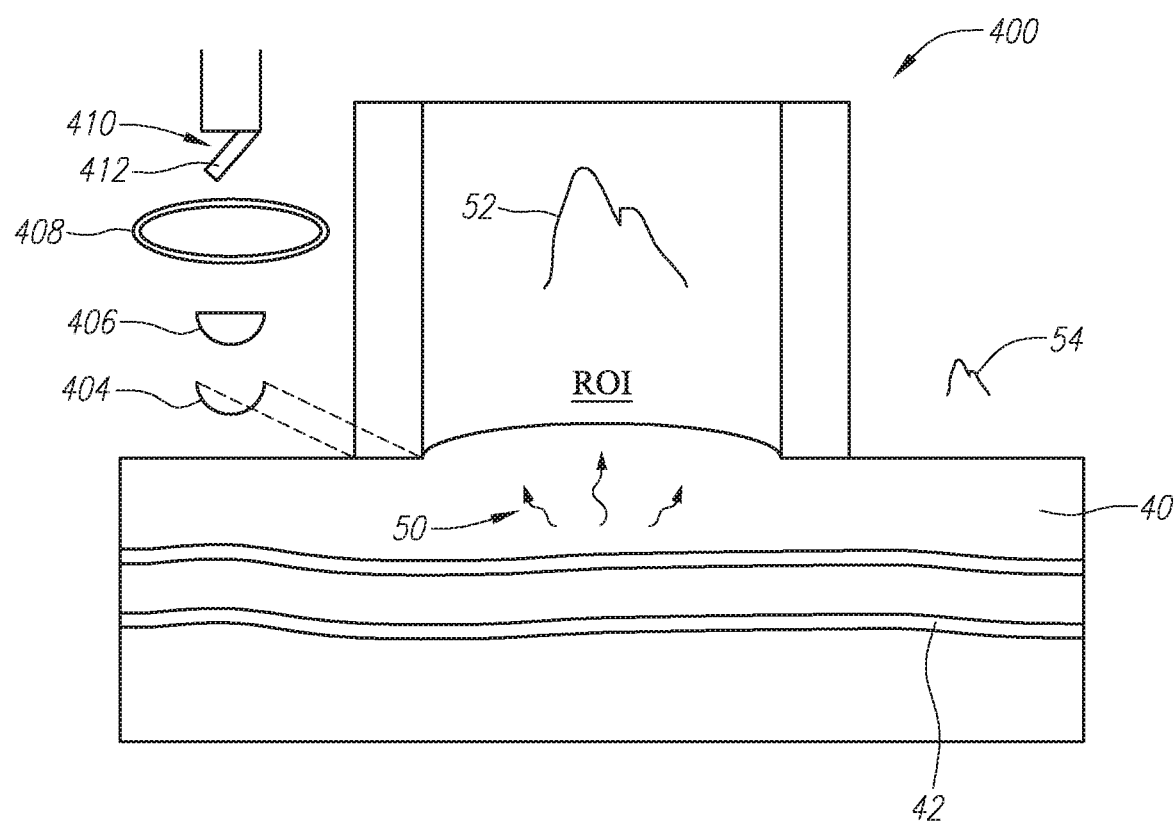
FIG. 6 is a cross-section view including optional skin-tensioning and signal-amplification hardware.

FIG. 6 details further optional aspects of the so-called amplification ring 400. Note, however, that this system element need not be "ring" shaped. In one embodiment (i.e., as shown), the structure is a hollow cylinder. In another embodiment, the structure is not a cylindrical but two barriers. In another embodiment, the structure is square in shape. While any number of geometries are possible depending on the region of interest and physiological signal, the exact geometry of the structure is left up to those skilled in the art.

In any case, FIG. 6 discloses hardware and a method for tensioning a material surface and/or underlying tissue or material to amplify motion as a wave is transferred from one medium to another. This method can be applied to tension the skin to increase the sensitivity of noninvasive physiological measurements. Generally, this method involves placing a structure 400 on top of the skin 40 of a subject with an artery 42 passing beneath. The structure channels the energy of a physiological signal 50—in this case pressure waveforms as function p(x,t) generated by the dynamics of the heart and arterial tree—within a region of interest "ROI". As such, an amplified waveform 52—as compared to lesser amplitude waveform 54 outside structure 400—may be captured.

Structure 400 may also include accessories or modifications to enhance performance as well as increase comfort. In one embodiment, the cylinder has a rounded edge 404. In another embodiment, the structure has a silicone or soft rubber bumper 406 at its distal interface (i.e., positioned as indicated for element 404). This bumper is able to deform to further tension skin. In another embodiment, the bumper is in the form of an O-ring 408. In another embodiment, the bumper is cross-sectionally formed to include a hinge 410 utilizing lever or rim 412 action to increase tension on the skin.

Figure 7A:
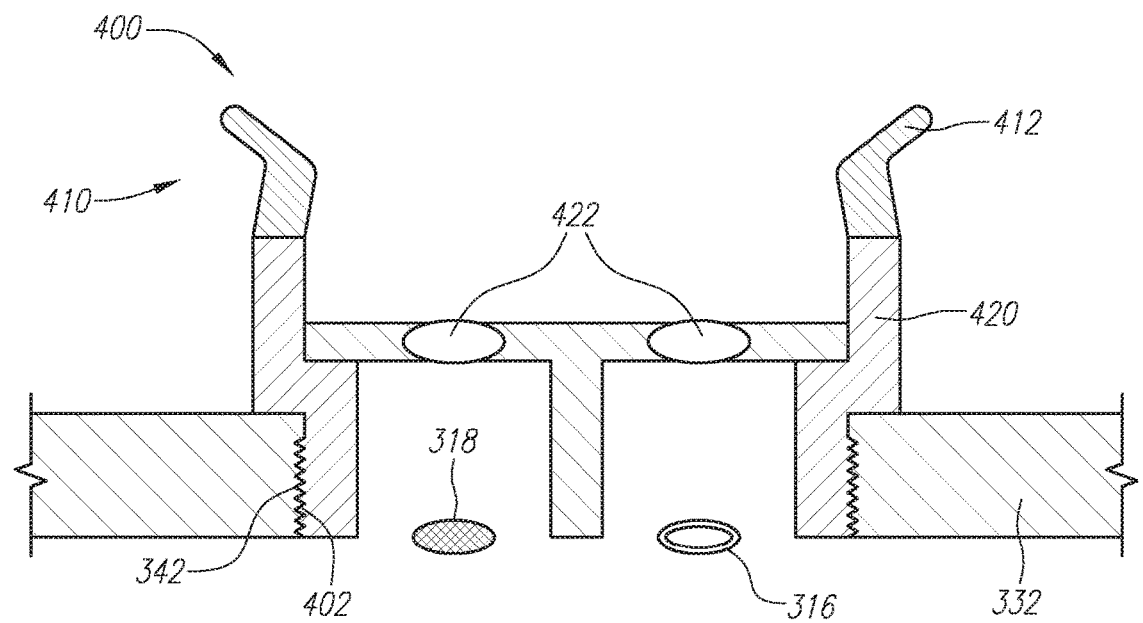
FIGS. 7A and 7B are cross-section views illustrating use of one of the skin-tensioning variation in connection with the embodiment illustrated in FIGS. 5A and 5B.
Figure 7B:
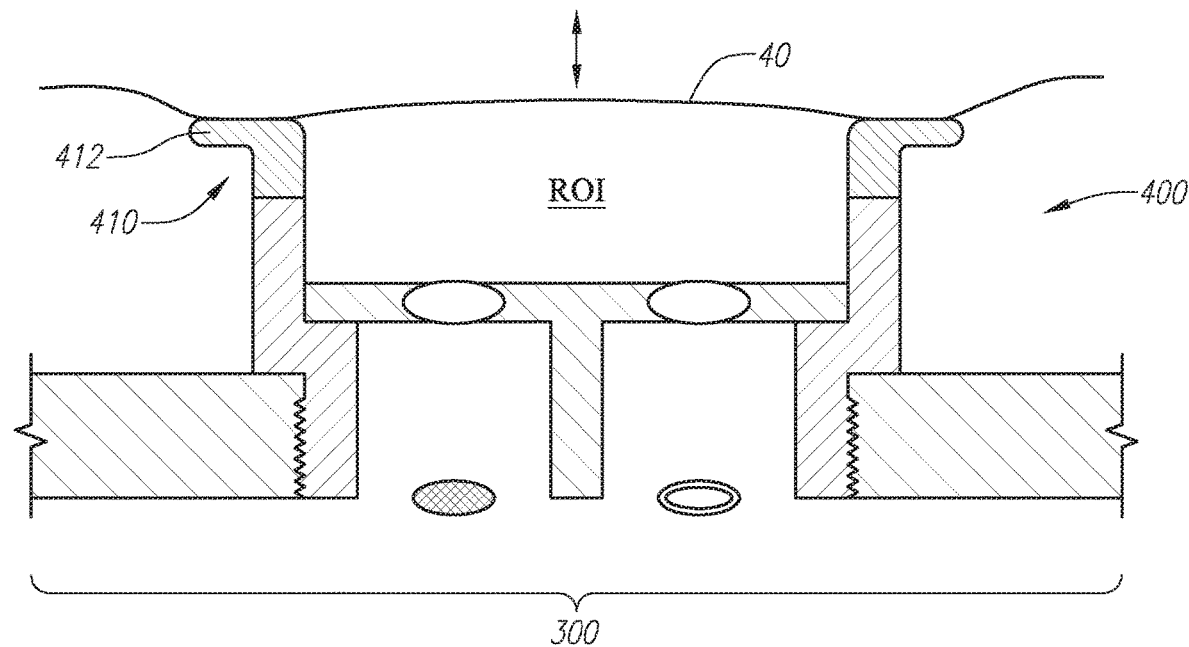

FIGS. 7A and 7B further illustrate this last variation. Here, hinging and lever action is accomplished as evident comparing the views once the rim or lever sections 412 are in contact with a subject's skin 40. As shown in FIG. 7B, the system is intended to measure movement or micro-movement (as indicated by the double-arrow) of the skin set within or surrounded by the ROI. A complementary threaded interface 342/402 is also shown securing a body 420 of the amplification ring to a/the smartphone case body 332. Alternatively, such an interface may be incorporated into a smartphone or another device. Amplification structure 400 may include lens and/or filter elements 422 for an associated device sensor 316 (be it a CMOS or CCD- or other light sensor) and LED 318 (or other light source) in an overall system 300.

Figure 8A:
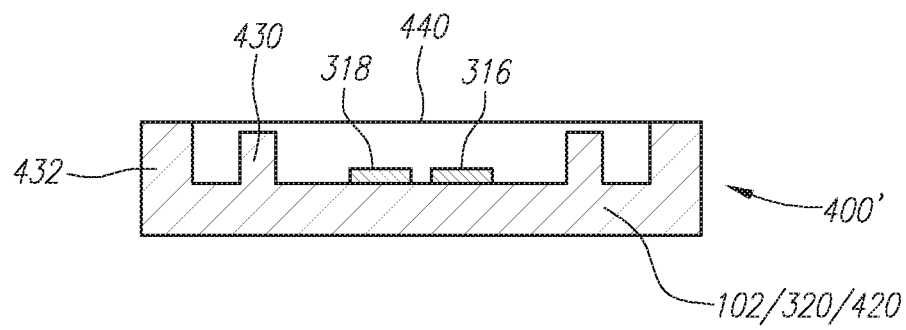
FIGS. 8A-8C are cross-section views illustrating use of another of the skin-tensioning variation that includes a sensor membrane.
Figure 8B:
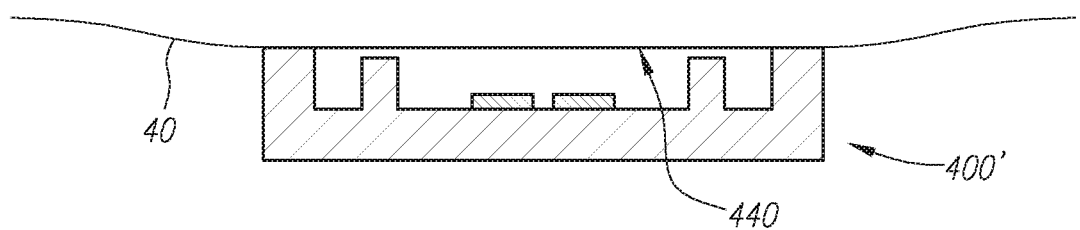
Figure 8C:
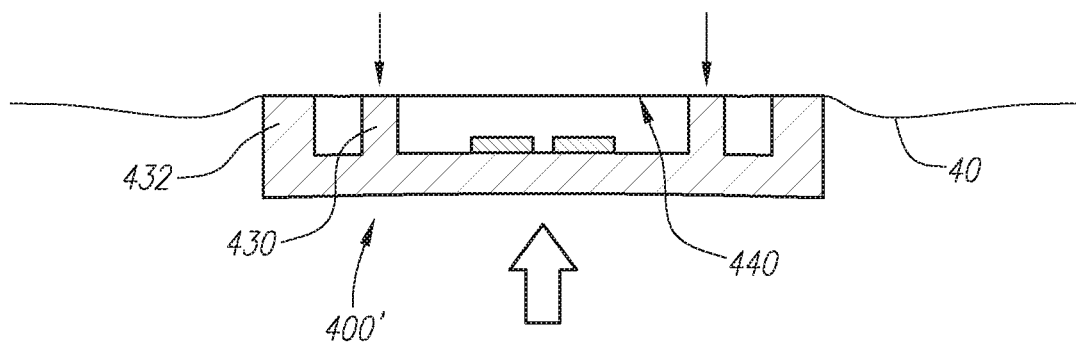

In another amplification structure 400' embodiment, concentric cylinders are used to provide tensioning and amplification. FIGS. 8A-8C illustrate such an approach. Here, structure 400 included concentric rings 430, 432. These rings may be included in the body or base 102 of an auxiliary sensor device, a body 320 of a smartphone device or the body 420 of an add-on amplifier structure like that in the preceding figures. Regardless, the interaction between a subject's skin 40 and the inner and outer rings 430, 432 stretch the skin as shown in FIGS. 8B and 8C.

In FIG. 8B, initial contact with made with the skin along the outer ring 432. Then, in pressing the structure 400' as indicated by the larger arrow, contact is achieved at/around the inner ring 430 stretching the skin and/or a membrane 440 interface incorporated in the structure.

Use of a membrane 440 as in the above embodiment enables further light-selective methodologies. Optical properties of the membrane are advantageously chosen such that it reflects at the wavelength of the LED back to the device sensor as well as blocks noise caused by ambient light. These results may be achieved by coloring and/or metalizing a polymer membrane (inside and/or out) via Chemical Vapor Deposition (CVD) or otherwise. Additionally, the membrane serves the purpose of increased robustness to user skin tone and body topography.

Figure 9:
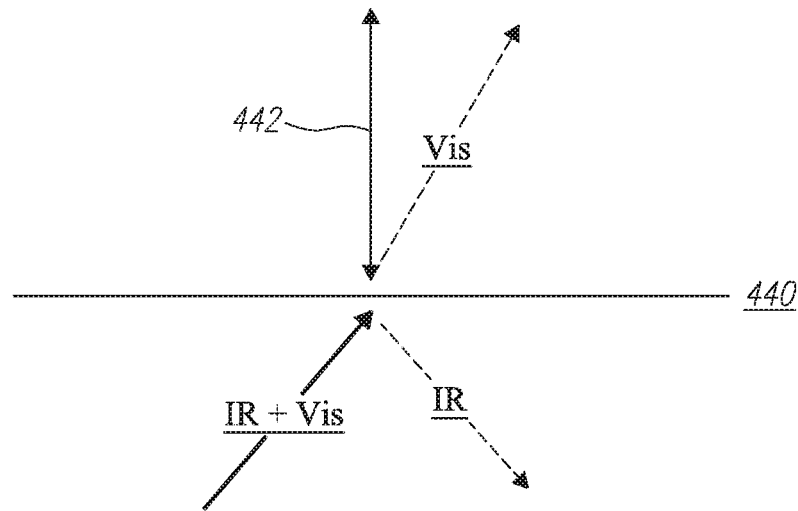
FIG. 9 is a diagram illustrating optical properties of a selected sensor membrane.

These concepts are illustrated in connection with FIG. 9. Here, exterior ambient light 442 from any source is reflected. It may also be desirable that light from an internal source (such as a/the LED 418) pass its visible (Vis) spectrum component(s) through membrane 440 and only reflect its Infrared (IR) component to a/the sensor. Such an approach can help reduce signal nose.

Most important is that external light does not pass through the membrane to the interior of the device where the sensor(s) are located. As such, the metalized surface may desirably set to the outside of the device where it reflects ambient light out or outward. As such, such an arrangement keeps all the internal light inside the device.

Whether incorporated in an amplification "ring" structure 400/400' or simply set in or across a sensor aperture or window 340 a/the membrane 440 may comprise any number of materials such as metals, plastics, animal skin and/or rubber. It advantageously comprises polyester or polyurethane. Physical parameters of the membrane are chosen to exhibit mechanical properties which allow the membrane to follow the pulse waveform. As such, membrane thickness is typically in the range of 12-500 µm with a diameter ranging from 1 mm to 50 mm.

As variously discussed, one application of the hardware and subject methodology is for arterial waveform measurement. In this regard, the amplified motion of the skin correlates to the pressure driven expansion of an artery. The amplified motion can therefore subsequently be recorded through any number of non-invasive transducers such as piezoelectric, capacitive, piezoresistive, optical, acoustic, ultrasound or electromagnetic. Similar techniques may be applied to measure physiological wave information that exists at different frequencies such as arterial waves versus phonocardiograms. The signal can be recorded using an optical reflective light sensor (e.g., with sensor 112 or 316). In another embodiment, a combination or array of these structures may be used to probe local arterial mechanical properties.

In the embodiment noted above, the amplification structure is housed in a mobile phone case or employed as a (direct) mobile phone attachment. In another embodiment, such a structure 400/400' could be built directly into the body or housing of the phone. In another embodiment, the structure is placed in a peripheral and/or portable device.

Figure 10A:
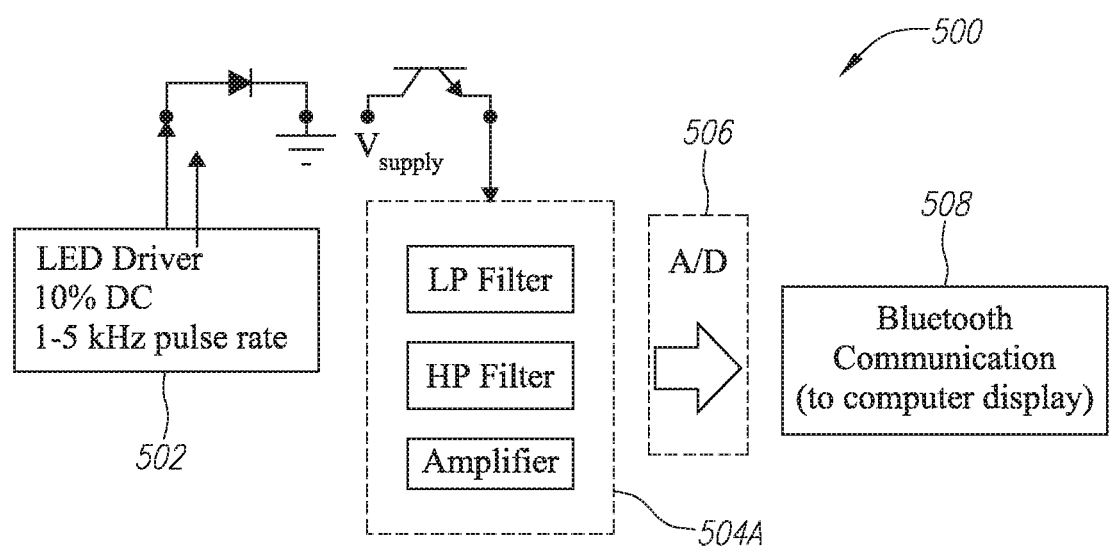

In any case, system componentry for optical embodiments for hemodynamic waveform acquisition are shown in FIGS. 10A and 10B. These systems 500 (as may be incorporated in those above) include an LED driver in functional block 502.

A functional block 504A in FIG. 10A for the diode/LED includes each of Low Pass (LP) filter, a High Pass (HP) filter and an Amplifier. A functional block 504B in FIG. 10B, again, for the diode/LED includes each of a band bass (BP) and low pass (LP) filter and Amplifier. Via an analog-to-digital (A/D) converter 506, the signal captured may be passed by a communication block 508 (e.g., through BLUETOOTH protocol) to a computer or handheld device 200 display or other electronic hardware for processing as variously described herein.

As to the different filtering options (i.e., differences apparent between blocks 504A and 504B), note that the HP filter in FIG. 10A is substituted for the BP filter in FIG. 10B. A BP filter may be used in case of a large DC offset present in the signal. However, an AC signal may be used, coupled with a LP filter. AC coupling is loosely analogous to a very low frequency HP filter. In which case, the figures may be viewed as analogous. All of the filtering may also all be done digitally. Stated otherwise, the filtering and DC offset removal can be done in the digital or analog domain. Likewise, DC offset removal, HP filtering, LP filtering and amplification can be done in parallel or in series.

Referring to FIGS. 11A and 11B, these figures show a blood vessel 42 and skin section 40. Radial distension from blood pressure is pictured in vessel 42 in FIG. 11A, and up-and-down movement of the skin 40 in the side view of FIG. 1B.

Figure 12:
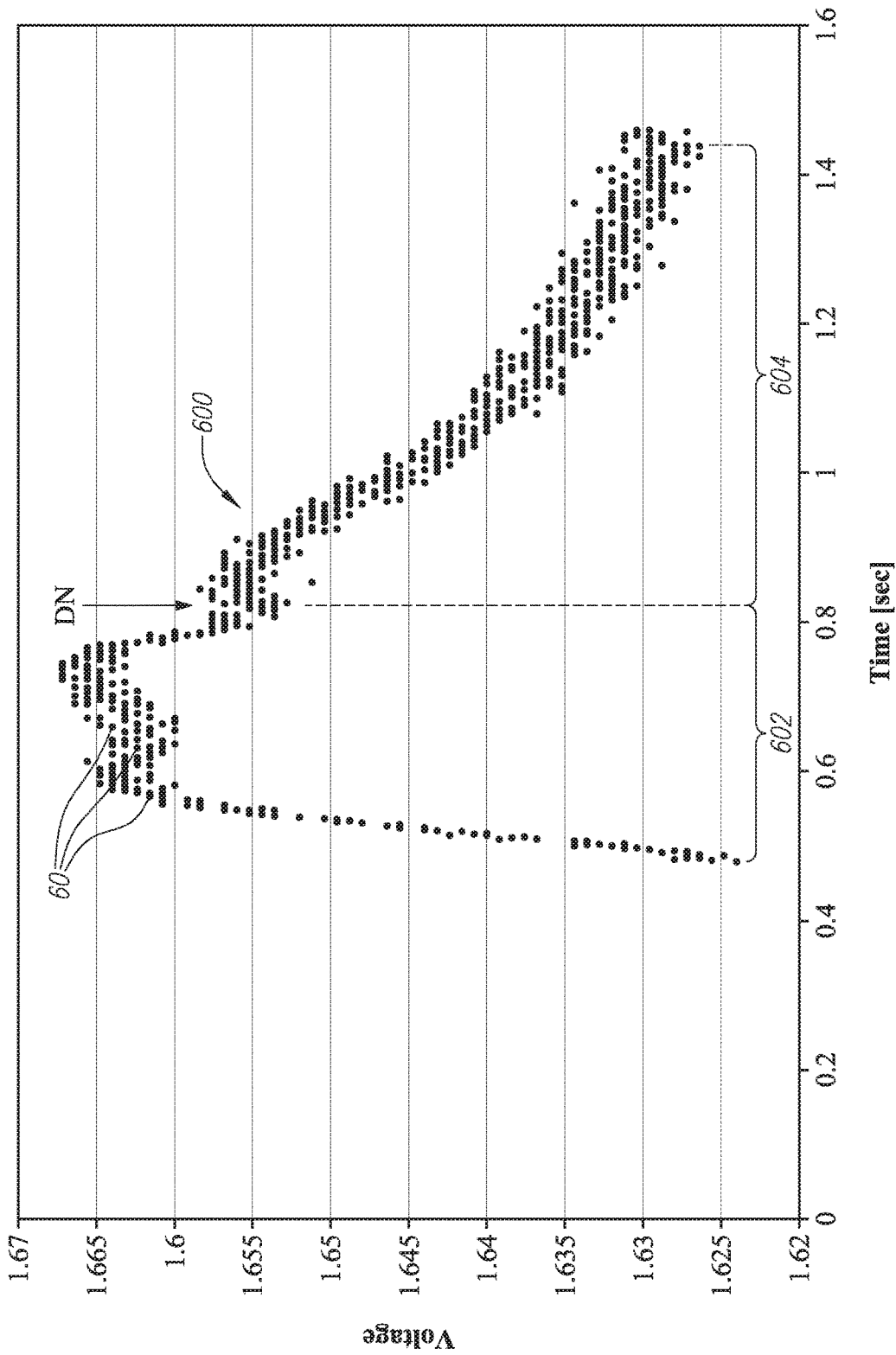
FIG. 12 is a chart showing optically acquired hemodynamic data.

Representative data optically captured from such movement is shown as by data points 60 in FIG. 12 generating a 600 hemodynamic waveform. As this data may be variously smoothed and processed into a discrete curve (as shown in other views herein), with a first section or a first section/domain 602 in which the heart and aorta are in a coupled system 10 and a second section/domain 604 for the aorta in a system 10' alone as in FIGS. 1A and 1B. These domains are delineated (or separated) by the Dicrotic Notch (DN) as shown.

Pulse Waveform and Embedded Frequency Acquisition

Using the subject hardware, a second set of frequencies corresponding with the heart sounds (the "Embedded Frequencies") are embedded within an arterial blood pressure waveform. As such, two different types of waveform can be obtained from the same location using the same device. Currently, tonometers for measuring blood pressure waveforms based on pressure sensors cannot or do not detect the Embedded Frequencies. Also, known stethoscopes (digital or otherwise) can detect heart sound, but they cannot or do not detect arterial blood pressure waveforms. This situation may be due to low-pass and high-pass filtering employed in the devices as a matter of course or design.

In any case, embodiments of the subject hardware and/or software discard neither signal. Rather, a vibrational signal on the skin of a patient is obtained and the signal is resolved in into each of a pulse pressure waveform and an Embedded Frequency signal. Doing so makes a number of techniques practical in application, even for a patient to self-administer.

As shown in FIG. 13A, each of a hemodynamic waveform (i.e., pulse pressure waveform) 610 and an Embedded Frequency waveform 612 have been detected and resolved into discrete signals.

Although other filters may be used, such resolution is preferably achieved by high-pass and/or low-pass filtering using Fourier transforms. Low-pass filtering yields the true pulse pressure waveform. High-pass filtering yields the true Embedded Frequency (or heart sound). Current filtering is set with High-pass about 20 Hz and Low-pass at about 250 Hz.

In some examples, a second derivative may be taken of the vibrational signal for this purpose. However, Fourier transform filtering may generally be preferred as a more accurate form of filtering. Whereas a second derivative will tend to amplify noise, a filter can cut it back, thus providing more accurate "character" of a sound. In other words, use of a classical filter (such as one based on Fourier transform) may be advantageous because it does not artificially amplify higher frequencies thereby making it easier to analyze a high pass signal—the Embedded Frequency in this case.

Signals 610 and 612 were captured together as one vibration signal detected with an optical sensor embodiment including a membrane as discussed above. This example was generated from measurements taken at the carotid artery (e.g., a pictured in FIG. 2) although other locations peripheral to the heart (e.g., femoral or radial) would yield similar results.

The Embedded Frequency signals present at least three properties. The properties open-up various opportunities of interest.

First, it has been observed that the Embedded Frequencies maintain the signature of the heart sound (i.e., they have the same profile or characteristics as sound waves originating at the heart). Accordingly, the signals can be used for cardiac auscultation.

Second, the Embedded Frequency signals maintain a constant distance from the beginning of the arterial blood pressure waveform to its Dicrotic Notch (DN). In contrast, sound waves measured at the heart travel throughout the body instantaneously making it difficult to use heart sounds to approximate the opening and closing of the aortic valve relative to a pressure waveform measurement (because the pressure waveform is offset from the instantaneous heart sound at peripheral locations). But because the Embedded Frequency signals travels with the arterial blood pressure waveform, they keep a unique synchronicity or timing property with the arterial blood pressure waveform allowing for easy detection of the DN. As such, the closing of the aortic valve (i.e., setting the location of the DN as indicated in FIG. 13A) can possibly be resolved even with a nondescript hemodynamic signal 620 as shown in FIG. 13B. This can be of great benefit, especially in accurately parsing a hemodynamic pulse pressure signal 600 into its constituent parts 602 and 604 on either side of the DN for IF analysis. Indeed, any cardiac cycle detection and/or segmentation of heart waveforms is potentially aided by the use of Embedded Frequencies. In general, timing related to arterial blood pressure waveforms can now be accomplished using the Embedded Frequencies instead of or in combination with arterial blood pressure waveforms.

Third, the travel time of the Embedded Frequencies with the pulse pressure waveform enables simplified methods of determining Pulse Wave Velocity (PWV) and/or Systolic Time Interval (STI) as elaborated in the Examples below.

Generally, the subject hardware and associated Embedded Frequency methodology opens opportunities for physiological/hemodynamic calculation and property quantification. The ability to capture both hemodynamic waveform and Embedded Frequency signal while eliminating the need of separate tonometer and stethoscope hardware and/or sensing locations offers various advantages. Moreover, the incorporation of multi-sensor technology (e.g., by including various ECG signal acquisition options in the sensing device or system) provides further synergy and opportunities.

Sampling Location Optimization

Figure 14A:
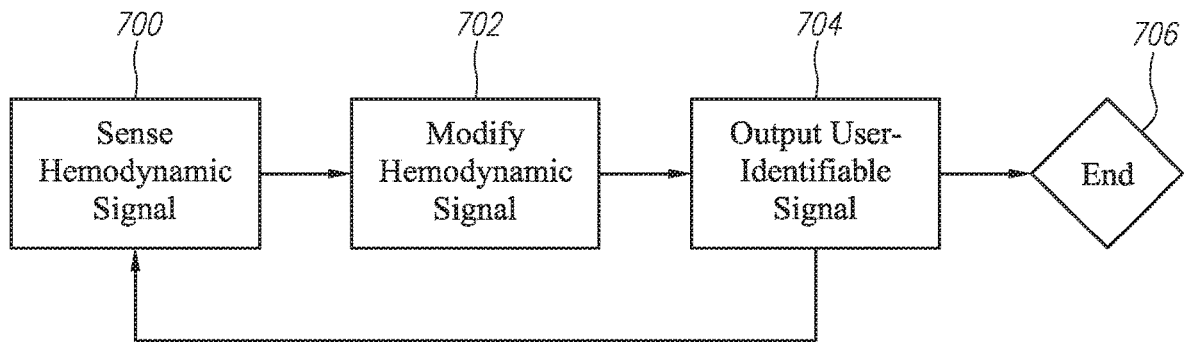
FIGS. 14A-14C are flowcharts illustrating various sampling localization optimization approaches.
Figure 14B:
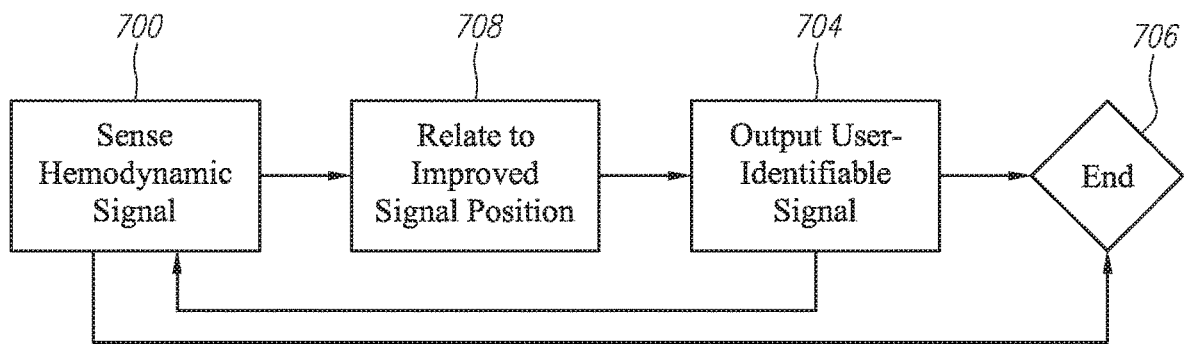
Figure 14C:
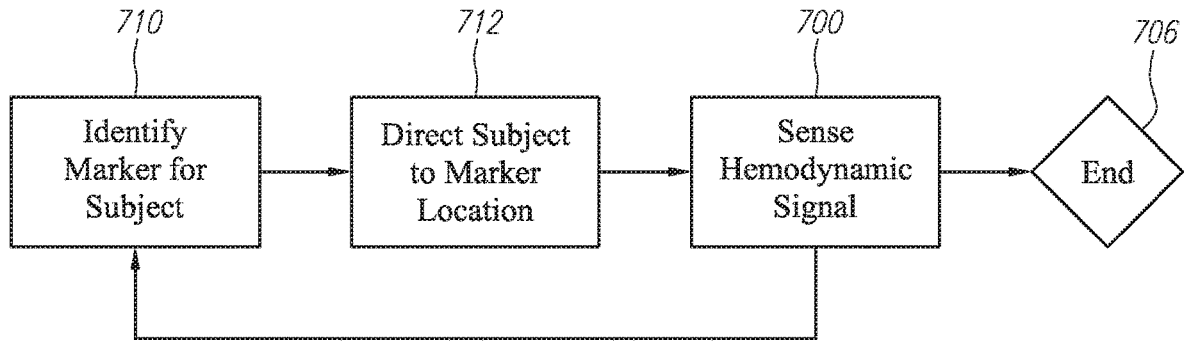

As referenced above, sensor location is important for good signal acquisition. Accordingly, a number of techniques for identifying optimal sensor location are provided. FIGS. 14A-14C illustrate various examples of methods (optionally, medical methods) and software routines or techniques. As noted, these techniques may be integrated into the UI of the subject devices and/or accomplished through interaction with a peripheral marker, beacon or service.

In one set of UI embodiments noted above, auditory and or visual signal(s) for a user are assigned to information streaming from a/the camera in the sensor device platform. As shown in FIG. 14A in more general terms, a hemodynamic signal is sensed at 700. This signal is modified or manipulated at 702 in any of various ways possibly described above or others, then output as a user identified or identifiable signal at 704. Such signaling may be auditory (e.g., as in from resolution to an intelligible signal out of noise, as from nothing to hearing a signal, as in an accelerated beeping to achieve a "lock," etc.) or visual (e.g., as indicated by light blinking or intensity, as gauged by a meter, etc.) as described above or otherwise. As the user moves the sensor device the process continues as indicated by the loop line until the user is directed by device feedback to a location where adequate signal is obtained and the process ends at 706.

In another set of UI embodiments, a method may be carried out in connection with a locator system as illustrated in FIG. 14B. In which case, sensing may begin at one position at 700. Using directional microphones or other techniques, this position can be related to more optimal position at 708 and then the user directed accordingly (such as by above or otherwise) at 704 as he or she moves towards or away from a more optimal position for sensing. As indicated, repeated signaling and sensing may be required. When an adequate signal is sensed and recorded, the process may end at 706.

In yet another set of UI embodiments, locating the sensor device for optimal signal acquisition may be achieved in connection with a constant marker as illustrated in FIG. 14C. In which case, the system may identify the marker (i.e., not usually viable to the user as discussed above) at 710. Then via various user-identified signal options (per above or otherwise) direct the user to the marker location at 712. Upon achieving desired location, sensing may then occur at 700 after which the process ends at 706. If optimal placement has not been achieved, however, or if multiple nearby sampling points are desired then the method may be run repeatedly or recursively with either goal in mind (i.e., for more accurate home-in to the marker and/or scattered sampling adjacent the marker point).

EXAMPLES

The subject systems have been discussed above as capable of delivering hemodynamic waveform data optically by acquisition with a smartphone in connection with its LED flash element and an LED phototransistor pair. Such data may be smoothed or averaged in connection with a graphical UI.

With reference to FIG. 4B, a carotid pressure waveform 800 is shown as recorded using an IPHONE camera and LED per above (although FIGS. 4A and 4B illustrate another smartphone hardware option). On display 320, a complete cardiac cycle 802 has been marked by three colored circular markers in the following sequence: red 804, white 806 and blue 808 (whereas this particular color scheme was created to cause the user to infer a particular—familiar—order as red being first, white second and blue third.) In this case, the time duration between the red and blue markers is the period of the cardiac cycle.

Display 320 also shows a Heart Rate (HR) of 60.03 bpm and $\omega_1=100$ and $\omega_2=50.4$ calculated using a/the Cloud 210 computing service. Then utilizing the approach described in U.S. patent application Ser. No. 14/517,702, ejection fraction for the exemplary measurements was produced yielding a result of 68%. This result offered good agreement with an ejection fraction of 64% for the same patient as measured by a biplane echo. In another example, $\omega_1$ and $\omega_2$, were calculated (also using a/the Cloud service) as 93.63 and 29.6, respectively, with a HR of 94.84 as shown in FIG. 3.

In each example (but described further in reference to FIG. 4B), the individual color-coded points in the waveform (s) can be selected using a combination of the markers and the "plus" and "minus" buttons 810. In one embodiment, a finger tap selection on the graph frame displaying the waveform auto-locates the markers based on the marker selected and the location of the tap relative to the graph frame. In another embodiment, the points are advanced into position using a slider. In another embodiment, the markers on the waveform can be dragged from sample to sample. In yet another embodiment, gestures or voice commands may be used to increment the markers in either direction. The markers can be stepped through the points on the waveform my clicking the plus and minus buttons. This sequence corresponds to the start, Dicrotic Notch (DN) as well as the end of a complete cardiac cycle and are the three inputs in addition to the data required by the intrinsic frequency algorithm.

These features are important to delivering a feel of control to the user given limited screen size of portable devices and the size of a finger or handheld stylus, particularly when high sampling rates are used. Since picking the points can affect the diagnostic outcome this UI control is a required feature. Additionally, this UI feature allows a balance between accurate point selection of the cardiac cycle while allowing the user a visual reference to larger features of the waveform. Also, the ability to manually confirm or select points can avoid any automatic selection that errors in selecting the DN, which can be difficult with previously known techniques.

However, an example herein provides a reliable means of determining the DN position or location within the subject hemodynamic waveform data. Namely, with data acquired from systems capable of detecting and/or filtering for an Embedded Frequency signal, as seen in FIG. 13A, it has been observed that the portion Embedded Frequency 612 created during the closing of the aortic valve remains a time interval ("t") approximately 40 milliseconds behind the Dicrotic Notch (DN) of the blood pressure waveform 610. In practice, the exact amount of delay or the exact feature of the S2 that we look at depends on the filter itself. Generally, there is a delay (e.g., about 4 to about 40 milliseconds) behind the notch. This slight delay will be dependent (but consistent) on the filter qualities. As such, the Embedded Frequency provides a computationally efficient and reliable indication of where the DN of the blood pressure waveform is located.

In another example, the subject hardware can be used for determining Pressure Wave Velocity (PVW). In which case, the hardware will include ECG sensor contact or lead electrodes. To make the determination, an ECG and the heart sound is recorded at the location of the heart and then ECG is measured again while the Embedded Frequency (heart sound) is recorded at a peripheral location (e.g., the carotid artery). By measuring distance between the location of the heart and the location of the subject device and the time it takes for the Embedded Frequency signal to travel from the heart to the selected peripheral location artery (timing each off of the ECG signal which is travels through the body instantaneously), then the speed at which the blood pressure wave travelled can be mathematically determined.

In another example, the subject hardware can again be used for determining Pressure Wave Velocity (PVW). In which case, the hardware will include an external microphone. To make the PWV determination, first the heart sound is recorded at the location of the heart while, simultaneously, the Embedded Frequency (heart sound) is recorded at one peripheral location (e.g., the carotid artery) using the subject hardware. Then, the heart sound is recorded at the location of the heart while, simultaneously, the Embedded Frequency (heart sound) is recorded at a different one peripheral location (e.g., the femoral artery) using the subject hardware. By measuring the distance between the two peripheral locations and the time it takes for the Embedded Frequency signal to travel from the heart to the selected peripheral locations (timing each off of the heart sound recorded at the location of the heart), then the speed at which the blood pressure wave travelled can be mathematically determined to measure, for instance, carotid-femoral or carotid-brachial pulse wave velocity. Alternatively, to measure ascending or descending aortic pulse wave velocity, first the heart sound is recorded at the location of the heart while, simultaneously, the Embedded Frequency (heart sound) is recorded at one peripheral location (e.g., the carotid, brachial, radial or femoral artery) using the subject hardware. By calculating the distance between the heart and the peripheral location where the measurement is taken one can mathematically determine ascending or descending aortic pulse wave velocity.

The subject hardware may also be used in connection with Embedded Frequency signal detection to provide a new approach to measuring systolic time intervals. Systolic time intervals have been measured using ECG, phonocardiogram and arterial blood pressure waveforms. In the past, three different devices at three different locations were used for this purpose. Using Embedded Frequencies according to the teachings herein, it is now possible to take measurements for calculating systolic time intervals with a single device and/or in a single location. In the subject technique, the sound waves used in prior systolic time interval calculations (e.g., *Circulation,* 1968; 37, 150) are replaced by the Embedded Frequencies measured. In which case, as indicated in FIG. 13C:

$$PEP = QS_2 - LVET \quad (1)$$

$$ICT = S_1S_2 - LVET \quad (2)$$

$$Q-1 = QS_2 - S_1S_2 \quad (3)$$

where $QS_2$ is the total electromechanical systole, $S_1S_2$ is the heart sounds interval (in this case found by Embedded Frequency signal measurement), LVET is left ventricular ejection time, PEP is total electromechanical systole, Q–1 is the interval from onset of QRS to the first heart sound, and ICT is isovolumic contraction time.

In another example, Ejection Fraction is determined using PEP as calculated above and the following equation adapted from *Circulation,* 1970; 42: 457:

$$EF = 1.125 - 1.25 \, PEP/LVET \quad (4)$$

where EF is ejection fraction and the PEP and LVET parameters are defined above. As such, EF is efficiently and accurately calculated on a basis including the subject Embedded Frequency signal acquisition systems and methods.

Variations

In addition to the embodiments that been disclosed in detail above, still more are possible within the classes described and the inventors intend these to be encompassed within this Specification and claims. This disclosure is intended to be exemplary, and the claims are intended to cover any modification or alternative which might be predictable to a person having ordinary skill in the art.

Moreover, the various illustrative processes described in connection with the embodiments herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information including a program that operates under control of the processor and with communication via the user interface port, and a video output that produces its output via any kind of video output format, e.g., VGA, DVI, HDMI, DisplayPort, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein. The camera may be a digital camera of any type including those using CMOS, CCD or other digital image capture technology.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on, transmitted over or resulting analysis/calculation data output as one or more instructions, code or other information on a computer-readable medium. Computer-readable media includes both computer storage media and communication media including any medium that facilitates transfer of a computer program from one place to another. A storage media may be any available non-transitory media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

All embodiments disclosed herein are intended for use with memory, storage, and/or computer readable media that is non-transitory. Accordingly, to the extent that memory, storage, and/or computer readable media are covered by one or more claims, then that memory, storage, and/or computer readable media is only non-transitory.

Operations as described herein can be carried out on or over a website. The website can be operated on a server computer or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Also, the inventors intend that only those claims which use the words "means for" are intended to be interpreted under 35 USC 112(f). Moreover, no limitations from the specification are intended to be read into any claims, unless those limitations are expressly included in the claims. The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, it is contemplated that any optional feature of the embodiment variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The invention claimed is:

1. A system comprising:
   a vibration sensor configured to capture a vibrational signal comprising frequency components, wherein the vibration sensor is configured to capture the signal from skin of a subject at a location peripheral to a heart of the subject;
   a processor; and
   a memory on which is stored a plurality of instructions that, when executed by the processor, cause the processor to:
   apply a low pass filter to resolve a pulse waveform, wherein application of the low pass filter passes frequency components of the vibrational signal from zero hertz to a low pass cutoff frequency of the low pass filter;
   apply a high pass filter to resolve Embedded Frequency signals corresponding to sound of the heart, wherein application of the high pass filter passes frequency components of the vibrational signal above a high pass cutoff frequency of the high pass filter; and
   calculate, using both the Embedded Frequency signals and the pulse waveform, at least one physiological parameter, wherein the physiological parameter is selected from at least one of Dicrotic Notch (DN) position of the pulse waveform, Ejection Fraction (EF) and systolic time intervals, and wherein the instructions are further adapted to cause the processor to calculate Intrinsic Frequency (IF) parameters $\omega 1$ and $\omega 2$ on each side of the DN.

2. The system of claim 1, wherein the low pass cutoff frequency is 250 hertz.

3. The method of claim 1, wherein the low pass filter is configured to resolve a pulse waveform having a frequency range of zero to 250 hertz.

4. The system of claim 1, wherein the vibration sensor comprises a light source and a light sensor.

5. The system of claim 4, wherein the light source is an LED in a smartphone camera.

6. The system of claim 4, wherein the vibration sensor further comprises a membrane, the membrane made of a material selected to be at least partially reflective to the light source on an inner surface of the membrane.

7. The system of claim 6, wherein the membrane comprises metal or is metalized on the inner surface.

8. The system of claim 6, wherein the membrane material is selected to reduce light passing from an outer surface of the membrane to the sensor.

9. The system of claim 8, wherein the material substantially eliminates light passing from the outer surface.

10. The system of claim 8, wherein the membrane comprises metal or is metalized on the inner surface.

11. The system of claim 1, further comprising an electrocardiogram (ECG) sensor, wherein the processor is further adapted for producing an ECG signal.

12. The system of claim 1, wherein the computer processor is further adapted to calculate Ejection Fraction (EF) using the Embedded Frequency signals, the pulse waveform and an ECG signal.

13. The system of claim 1, further comprising a ring-shaped extension from a housing of the vibration sensor.

14. The system of claim 13, wherein the extension includes an outer ring and an inner ring, wherein the inner ring defines a ledge to limit skin depression.

15. A method comprising:
- capturing, with a vibration sensor on a subject's skin at a location peripheral to the subject's heart, a vibrational signal representative of skin vibration sensed by the vibration sensor, wherein the vibrational signal comprises frequency components;
- applying a low pass filter to resolve a pulse waveform, wherein applying the low pass filter comprises passing frequency components of the vibrational signal from zero hertz to a low pass cutoff frequency of the low pass filter;
- applying a high pass filter to resolve Embedded Frequency signals corresponding to sound of the heart, wherein applying the high pass filter comprises passing frequency components of the vibrational signal above a high pass cutoff frequency of the high pass filter;
- calculating with a computer processor, using both the Embedded Frequency signals and the pulse waveform, at least one physiological parameter; and
- calculating Intrinsic Frequency (IF) parameters $\omega_1$ and $\omega_2$ with the computer processor.

16. The method of claim 15, wherein the low pass cutoff frequency is 250 hertz.

17. The method of claim 15, wherein the low pass filter is configured to resolve a pulse waveform having a frequency range of zero to 250 hertz.

18. The method of claim 15, further comprising determining a Dicrotic Notch (DN) position within the pulse waveform using the Embedded Frequency signals with the computer processor.

19. The method of claim 15, further comprising calculating Ejection Fraction (EF) with the computer processor using $\omega_1$ and $\omega_2$.

20. The method of claim 15, wherein the vibration sensor includes a ring-shaped extension from a housing of the vibration sensor, and the method further comprises stretching the skin with the extension.

21. The method of claim 20, wherein the extension includes an outer ring and an inner ring, and the method further comprises limiting skin depression with the inner ring.

* * * * *